United States Patent
Ito et al.

(10) Patent No.: US 11,999,978 B2
(45) Date of Patent: Jun. 4, 2024

(54) ALKALINE PHOSPHATASE COMPOSITION, METHOD OF PRODUCING DEPHOSPHORYLATED NUCLEIC ACID AND METHOD OF PRODUCING LABELED NUCLEIC ACID

(71) Applicant: Toray Industries, Inc., Chuo-ku (JP)

(72) Inventors: Masateru Ito, Kamakura (JP); Yoji Ueda, Kamakura (JP); Yuki Takii, Kamakura (JP); Mai Yagi, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 673 days.

(21) Appl. No.: 17/279,686

(22) PCT Filed: Sep. 25, 2019

(86) PCT No.: PCT/JP2019/037519
§ 371 (c)(1),
(2) Date: Mar. 25, 2021

(87) PCT Pub. No.: WO2020/067121
PCT Pub. Date: Apr. 2, 2020

(65) Prior Publication Data
US 2021/0395708 A1 Dec. 23, 2021

(30) Foreign Application Priority Data

Sep. 25, 2018 (JP) ................. 2018-179533

(51) Int. Cl.
*C12N 9/16* (2006.01)
*C12P 19/34* (2006.01)

(52) U.S. Cl.
CPC ............... *C12N 9/16* (2013.01); *C12P 19/34* (2013.01); *C12Y 301/03001* (2013.01)

(58) Field of Classification Search
CPC .... C12N 9/16; C12P 19/34; C12Y 301/03001
See application file for complete search history.

(56) References Cited

U.S. PATENT DOCUMENTS

| | | | |
|---|---|---|---|
| 5,705,610 A | 1/1998 | Zuckermann et al. | |
| 6,406,899 B1 | 6/2002 | Hoelke et al. | |
| 7,037,659 B2 | 5/2006 | Cerrina et al. | |
| 2002/0155481 A1 | 10/2002 | Cerrina et al. | |
| 2007/0148140 A1 | 6/2007 | Kiss | |
| 2008/0098491 A1 | 4/2008 | Kiss | |

FOREIGN PATENT DOCUMENTS

| | | |
|---|---|---|
| JP | H10-503841 A | 4/1998 |
| JP | H10-262674 A | 10/1998 |
| JP | 3922454 B2 | 3/2007 |
| WO | 95/35505 A1 | 12/1995 |
| WO | 2012/115023 A1 | 8/2012 |
| WO | 2014/007229 A1 | 1/2014 |

OTHER PUBLICATIONS

First Office Action dated Aug. 11, 2023, of counterpart Chinese Patent Application No. 201980062602.0, along with an English translation.
Notice of Reasons for Refusal dated Sep. 5, 2023, of counterpart Japanese Patent Application No. 2019-554583, along with an English translation.
Extended European Search Report dated Jul. 1, 2022, of counterpart European Patent Application No. 19864706.7.
C. Pozidis et al., "Preparation of high purity alkaline phosphatase from calf intestine using dye-ligand chromatography," Bioseparation, vol. 5, No. 2, 1995, pp. 89-93 (Abstract, Introduction).

*Primary Examiner* — Robert J Yamasaki
*Assistant Examiner* — Trevor Kane
(74) *Attorney, Agent, or Firm* — DLA Piper LLP (US)

(57) ABSTRACT

A composition contains an alkaline phosphatase and first to sixth peptide fragments, wherein content ratios of the first to sixth peptide fragments to the alkaline phosphatase satisfy formulas (1) to (6), respectively: $(X_1/Y) \times 100 \leq 0.6000$ (1); $(X_2/Y) \times 100 \leq 0.1800$ (2); $(X_3/Y) \times 100 \leq 0.2000$ (3); $(X_4/Y) \times 100 \leq 0.8000$ (4); $(X_5/Y) \times 100 \leq 1.6000$ (5); and $(X_6/Y) \times 100 \leq 0.3500$ (6), wherein $X_1$ to $X_6$ represent peak area values of the first to sixth peptide fragments calculated by an automatic integration method from an extracted ion chromatogram obtained by an LC-MS/MS analysis of the composition, respectively, and Y represents a peak area value of the alkaline phosphatase calculated by an automatic integration method from a chromatogram obtained by an LC-UV analysis of the composition.

14 Claims, 10 Drawing Sheets
Specification includes a Sequence Listing.

```
                            SEQUENCE LISTING

<160> NUMBER OF SEQ ID NOS: 10

<210> SEQ ID NO 1
<211> LENGTH: 11
<212> TYPE: PRT
<213> ORGANISM: Bos taurus

<400> SEQUENCE: 1

Asp Arg Gln Val Pro Asp Ser Ala Gly Thr Ala
1               5                   10

<210> SEQ ID NO 2
<211> LENGTH: 9
<212> TYPE: PRT
<213> ORGANISM: Bos taurus

<400> SEQUENCE: 2

Ala Pro Gly Lys Ala Leu Asp Ser Lys
1               5

<210> SEQ ID NO 3
<211> LENGTH: 18
<212> TYPE: PRT
<213> ORGANISM: Bos taurus

<400> SEQUENCE: 3

Gly Pro Gln Ala His Leu Val His Gly Val Gln Glu Glu Thr Phe Val
1               5                   10                  15

Ala His

<210> SEQ ID NO 4
<211> LENGTH: 13
<212> TYPE: PRT
<213> ORGANISM: Bos taurus

<400> SEQUENCE: 4

Glu Gly Val Ser Leu Glu Lys Arg Glu Ala Glu Ala Glu
1               5                   10

<210> SEQ ID NO 5
<211> LENGTH: 13
<212> TYPE: PRT
<213> ORGANISM: Bos taurus

<400> SEQUENCE: 5

Val Pro Leu Ala Ser Glu Thr His Gly Gly Glu Asp Val
1               5                   10

<210> SEQ ID NO 6
<211> LENGTH: 12
<212> TYPE: PRT
<213> ORGANISM: Bos taurus

<400> SEQUENCE: 6

Gly Pro Gln Ala His Leu Val His Gly Val Gln Glu
1               5                   10

<210> SEQ ID NO 7
<211> LENGTH: 24
```

```
<212> TYPE: PRT
<213> ORGANISM: Bos taurus

<400> SEQUENCE: 7

Glu Ala Glu Ala Glu Phe Leu Ile Pro Ala Glu Glu Asn Pro Ala
1               5                   10                  15

Phe Trp Asn Arg Gln Ala Ala Gln
            20

<210> SEQ ID NO 8
<211> LENGTH: 16
<212> TYPE: PRT
<213> ORGANISM: Bos taurus

<400> SEQUENCE: 8

Val Pro Leu Ala Ser Glu Thr His Gly Gly Glu Asp Val Ala Val Phe
1               5                   10                  15

<210> SEQ ID NO 9
<211> LENGTH: 13
<212> TYPE: PRT
<213> ORGANISM: Bos taurus

<400> SEQUENCE: 9

Ile Pro Ala Glu Glu Asn Pro Ala Phe Trp Asn Arg
1               5                   10

<210> SEQ ID NO 10
<211> LENGTH: 578
<212> TYPE: PRT
<213> ORGANISM: Bos taurus

<400> SEQUENCE: 10

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe Leu Ile Pro Ala Glu
                85                  90                  95

Glu Glu Asn Pro Ala Phe Trp Asn Arg Gln Ala Ala Gln Ala Leu Asp
            100                 105                 110

Val Ala Lys Lys Leu Gln Pro Ile Gln Thr Ala Ala Lys Asn Val Ile
        115                 120                 125

Leu Phe Leu Gly Asp Gly Met Gly Val Pro Thr Val Thr Ala Thr Arg
    130                 135                 140

Ile Leu Lys Gly Gln Met Asn Gly Lys Leu Gly Pro Glu Thr Pro Leu
145                 150                 155                 160

Ala Met Asp Gln Phe Pro Tyr Val Ala Leu Ser Lys Thr Tyr Asn Val
                165                 170                 175

Asp Arg Gln Val Pro Asp Ser Ala Gly Thr Ala Thr Ala Tyr Leu Cys
            180                 185                 190

Gly Val Lys Gly Asn Tyr Arg Thr Asn Gly Lys Leu Gly Pro Glu Thr
        195                 200                 205
```

```
Pro Leu Ala Met Asp Gln Phe Pro Tyr Val Ala Leu Ser Lys Thr Tyr
    210                 215                 220
Asn Val Asp Arg Gln Val Pro Asp Ser Ala Gly Thr Ala Thr Ala Tyr
225                 230                 235                 240
Leu Cys Gly Val Lys Gly Asn Tyr Arg Thr Tyr Ala His Thr Val Asn
                245                 250                 255
Arg Asn Trp Tyr Ser Asp Ala Asp Leu Pro Ala Asp Ala Gln Lys Asn
            260                 265                 270
Gly Cys Gln Asp Ile Ala Ala Gln Leu Val Tyr Asn Met Asp Ile Asp
        275                 280                 285
Val Ile Leu Gly Gly Gly Arg Met Tyr Met Phe Pro Glu Gly Thr Pro
    290                 295                 300
Asp Pro Glu Tyr Pro Asp Asp Ala Ser Val Asn Gly Val Arg Lys Asp
305                 310                 315                 320
Lys Gln Asn Leu Val Gln Glu Trp Gln Ala Lys His Gln Gly Ala Gln
                325                 330                 335
Tyr Val Trp Asn Arg Thr Ala Leu Leu Gln Ala Ala Asp Asp Ser Ser
            340                 345                 350
Val Thr His Leu Met Gly Leu Phe Glu Pro Ala Asp Met Lys Tyr Asn
        355                 360                 365
Val Gln Gln Asp His Thr Lys Asp Pro Thr Leu Ala Glu Met Thr Glu
    370                 375                 380
Ala Ala Leu Gln Val Leu Ser Arg Asn Pro Arg Gly Phe Tyr Leu Phe
385                 390                 395                 400
Val Glu Gly Gly Arg Ile Asp His Gly His His Asp Gly Lys Ala Tyr
                405                 410                 415
Met Ala Leu Thr Glu Ala Ile Met Phe Asp Asn Ala Ile Ala Lys Ala
            420                 425                 430
Asn Glu Leu Thr Ser Glu Leu Asp Thr Leu Ile Leu Val Thr Ala Asp
        435                 440                 445
His Ser His Val Phe Ser Phe Gly Gly Tyr Thr Leu Arg Gly Thr Ser
    450                 455                 460
Ile Phe Gly Leu Ala Pro Gly Lys Ala Leu Asp Ser Lys Ser Tyr Thr
465                 470                 475                 480
Ser Ile Leu Tyr Gly Asn Gly Pro Gly Tyr Ala Leu Gly Gly Gly Ser
                485                 490                 495
Arg Pro Asp Val Asn Gly Ser Thr Ser Glu Glu Pro Ser Tyr Arg Gln
            500                 505                 510
Gln Ala Ala Val Pro Leu Ala Ser Glu Thr His Gly Gly Glu Asp Val
        515                 520                 525
Ala Val Phe Ala Arg Gly Pro Gln Ala His Leu Val His Gly Val Gln
    530                 535                 540
Glu Glu Thr Phe Val Ala His Ile Met Ala Phe Ala Gly Cys Val Glu
545                 550                 555                 560
Pro Tyr Thr Asp Cys Asn Leu Pro Ala Pro Ala Thr Ala Thr Ser Ile
                565                 570                 575
Pro Asp
```

ALKALINE PHOSPHATASE COMPOSITION, METHOD OF PRODUCING DEPHOSPHORYLATED NUCLEIC ACID AND METHOD OF PRODUCING LABELED NUCLEIC ACID

TECHNICAL FIELD

This disclosure relates to a composition containing an alkaline phosphatase, a method of producing a dephosphorylated nucleic acid by using the composition and a method of producing a labeled nucleic acid by using the composition.

BACKGROUND

An alkaline phosphatase has a catalyst function that hydrolyzes phosphoric monoesters, and has been widely used in methods of measuring the amount of biological substances such as proteins and nucleic acids (e.g., the immunostaining method, ELISA, the nucleic acid microarray method or the like). For example, in the research field of genetic engineering, for pretreatment of labeling of nucleic acids such as DNA and RNA and prevention of self-ligation of vectors, dephosphorylation of the 5' end and/or the 3' end of a nucleic acid with an alkaline phosphatase has been performed.

As an industrial production method of an alkaline phosphatase, a production method in which bovine small intestine or large intestine is mainly used as a raw material has been widely adopted since the specific activity of the produced alkaline phosphatase is high. The specific activity of an alkaline phosphatase is generally evaluated by measuring the absorbance at 405 nm derived from p-nitrophenol produced when p-nitrophenylphosphate is decomposed.

The quality of an alkaline phosphatase has been evaluated based on the alkaline phosphatase specific activity. To obtain an alkaline phosphatase having a higher specific activity than that of an alkaline phosphatase derived from bovine intestine, an alkaline phosphatase having a high specific activity has been isolated in a purification process or has been produced by using recombinant *Escherichia coli* obtained by a genetic engineering method.

JP H10-262674 A discloses a method of producing an alkaline phosphatase having a high specific activity by using recombinant *Escherichia coli* into which an alkaline phosphatase-encoding gene derived from the genus *Bacillus badius* has been introduced. WO 2012/115023 discloses a method of producing an alkaline phosphatase having a high specific activity and heat resistance by using recombinant *Escherichia coli* into which an alkaline phosphatase-encoding gene derived from the genus *Shewanella* has been introduced.

A dephosphorylation reagent containing an alkaline phosphatase (e.g., a commercially available alkaline phosphatase product) is a composition containing other components in addition to the alkaline phosphatase. A quality of a dephosphorylation reagent containing an alkaline phosphatase is evaluated based on the alkaline phosphatase specific activity.

However, we found that, even if labeled nucleic acids prepared by using dephosphorylation reagents having almost the same alkaline phosphatase specific activity (labeled nucleic acids obtained by dephosphorylating the 5' ends and/or the 3' ends of nucleic acids with the dephosphorylation reagents, and then binding labeling substances to the 5' ends and/or the 3' ends of the dephosphorylated nucleic acids) are used for a nucleic acid detection method, a great difference in the detection sensitivity between the labeled nucleic acids may occur in the nucleic acid detection method. In other words, we found that the quality of a dephosphorylation reagent containing an alkaline phosphatase cannot be evaluated correctly by using the alkaline phosphatase specific activity as an index.

Thus, it could be helpful to provide a composition containing an alkaline phosphatase and having a high quality, a method of producing a dephosphorylated nucleic acid by using the composition and a method of producing a labeled nucleic acid by using the composition.

SUMMARY

We found that the following impurities can coexist in a dephosphorylation reagent containing an alkaline phosphatase (e.g., a commercially available alkaline phosphatase product):

a first peptide fragment consisting of the amino acid sequence set forth in SEQ ID NO: 1;
a second peptide fragment consisting of the amino acid sequence set forth in SEQ ID NO: 2;
a third peptide fragment consisting of the amino acid sequence set forth in SEQ ID NO: 3;
a fourth peptide fragment consisting of the amino acid sequence set forth in SEQ ID NO: 4;
a fifth peptide fragment consisting of the amino acid sequence set forth in SEQ ID NO: 5;
a sixth peptide fragment consisting of the amino acid sequence set forth in SEQ ID NO: 6;
a seventh peptide fragment consisting of the amino acid sequence set forth in SEQ ID NO: 7;
an eighth peptide fragment consisting of the amino acid sequence set forth in SEQ ID NO: 8; and
a ninth peptide fragment consisting of the amino acid sequence set forth in SEQ ID NO: 9.

In addition, we have found that, by reducing, in a dephosphorylation reagent used to prepare a labeled nucleic acid (a labeled nucleic acid obtained by dephosphorylating the 5' end and/or the 3' end of a nucleic acid with the dephosphorylation reagent, and then binding a labeling substance to the 5' end and/or the 3' end of the dephosphorylated nucleic acid) for a nucleic acid detection method, the contents of the first to sixth peptide fragments (preferably, the contents of the first to sixth peptide fragments, and the content(s) of one, two or three peptide fragments selected from the group consisting of the seventh to ninth peptide fragments), it is possible to improve the detection sensitivity of the labeled nucleic acid in the nucleic acid detection method, thus completing this disclosure.

We thus provide:

[1] A composition containing:
an alkaline phosphatase;
a first peptide fragment consisting of the amino acid sequence set forth in SEQ ID NO: 1;
a second peptide fragment consisting of the amino acid sequence set forth in SEQ ID NO: 2;
a third peptide fragment consisting of the amino acid sequence set forth in SEQ ID NO: 3;
a fourth peptide fragment consisting of the amino acid sequence set forth in SEQ ID NO: 4;
a fifth peptide fragment consisting of the amino acid sequence set forth in SEQ ID NO: 5; and
a sixth peptide fragment consisting of the amino acid sequence set forth in SEQ ID NO: 6, wherein content ratios of the first to sixth peptide fragments to the alkaline phosphatase satisfy formulas (1) to (6), respectively:

$$(X_1/Y) \times 100 \leq 0.6000 \quad (1);$$

$$(X_2/Y) \times 100 \leq 0.1800 \quad (2);$$

$$(X_3/Y) \times 100 \leq 0.2000 \quad (3);$$

$$(X_4/Y) \times 100 \leq 0.8000 \quad (4);$$

$$(X_5/Y) \times 100 \leq 1.6000 \quad (5); \text{ and}$$

$$(X_6/Y) \times 100 \leq 0.3500 \quad (6),$$

wherein $X_1$ to $X_6$ represent peak area values of the first to sixth peptide fragments calculated by an automatic integration method from an extracted ion chromatogram obtained by an LC-MS/MS analysis of the composition, respectively, and Y represents a peak area value of the alkaline phosphatase calculated by an automatic integration method from a chromatogram obtained by an LC-UV analysis of the composition.

[2] The composition according to [1], wherein:
the composition further contains a seventh peptide fragment consisting of the amino acid sequence set forth in SEQ ID NO: 7; and
a content ratio of the seventh peptide fragment to the alkaline phosphatase satisfies formula (7):

$$(X_7/Y) \times 100 \leq 1.0000 \quad (7),$$

wherein $X_7$ represents a peak area value of the seventh peptide fragment calculated by an automatic integration method from an extracted ion chromatogram obtained by an LC-MS/MS analysis of the composition, and Y is the same as defined above.

[3] The composition according to [1] or [2], wherein:
the composition further contains an eighth peptide fragment consisting of the amino acid sequence set forth in SEQ ID NO: 8; and
a content ratio of the eighth peptide fragment to the alkaline phosphatase satisfies formula (8):

$$(X_8/Y) \times 100 \leq 1.0000 \quad (8),$$

wherein $X_8$ represents a peak area value of the eighth peptide fragment calculated by an automatic integration method from an extracted ion chromatogram obtained by an LC-MS/MS analysis of the composition, and Y is the same as defined above.

[4] The composition according to any one of [1] to [3], wherein:
the composition further contains a ninth peptide fragment consisting of the amino acid sequence set forth in SEQ ID NO: 9; and
a content ratio of the ninth peptide fragment to the alkaline phosphatase satisfies formula (9):

$$(X_9/Y) \times 100 \leq 2.3000 \quad (9),$$

wherein $X_9$ represents a peak area value of the ninth peptide fragment calculated by an automatic integration method from an extracted ion chromatogram obtained by an LC-MS/MS analysis of the composition, and Y is the same as defined above.

[5] The composition according to any one of [1] to [4], wherein the composition has an alkaline phosphatase specific activity of 2,000 U/mg or more.

[6] The composition according to any one of [1] to [5], wherein the alkaline phosphatase is selected from the following (a) and (b):
(a) an alkaline phosphatase containing a protein molecule consisting of the amino acid sequence set forth in SEQ ID NO: 10; and
(b) an alkaline phosphatase containing a protein molecule consisting of an amino acid sequence that has 70% or more sequence identity to the amino acid sequence set forth in SEQ ID NO: 10 and contains positions 78 to 90, positions 177 to 187, positions 469 to 477, positions 516 to 528 and positions 534 to 551 of the amino acid sequence set forth in SEQ ID NO: 10.

[7] The composition according to [6], wherein the amino acid sequence of the protein molecule of the alkaline phosphatase (b) further contains one or two or more selected from positions 91 to 109, positions 93 to 105 and positions 529 to 531 of the amino acid sequence set forth in SEQ ID NO: 10.

[8] The composition according to [6], wherein the amino acid sequence of the protein molecule of the alkaline phosphatase (b) further contains positions 91 to 109 and positions 529 to 531 of the amino acid sequence set forth in SEQ ID NO: 10.

[9] The composition according to any one of [1] to [8], wherein the composition further contains a nucleic acid.

[10] The composition according to [9], wherein the composition is a composition used for dephosphorylating the nucleic acid.

[11] The composition according to any one of [1] to [8], wherein the composition further contains a dephosphorylated nucleic acid.

[12] The composition according to [11], wherein the composition is a composition used for preparing a labeled nucleic acid containing the dephosphorylated nucleic acid and a labeling substance bound to the dephosphorylated nucleic acid.

[13] The composition according to any one of [1] to [8], wherein the composition further contains a labeled nucleic acid containing a dephosphorylated nucleic acid and a labeling substance bound to the dephosphorylated nucleic acid.

[14] The composition according to [13], wherein the composition is a nucleic acid sample to be subjected to a nucleic acid detection method.

[15] The composition according to [14], wherein the nucleic acid detection method is a nucleic acid detection method using a nucleic acid microarray.

[16] A method of producing a dephosphorylated nucleic acid, the method including steps of:
providing the composition according to any one of [1] to [8];
providing a nucleic acid; and
treating the nucleic acid with the composition to dephosphorylate the nucleic acid.

[17] A method of producing a labeled nucleic acid, the method including steps of:
providing the composition according to any one of [1] to [8];
providing a nucleic acid;
providing a labeling substance;
treating the nucleic acid with the composition to dephosphorylate the nucleic acid; and
binding the labeling substance to the dephosphorylated nucleic acid.

We provide a composition containing an alkaline phosphatase and having a high quality, a method of producing a dephosphorylated nucleic acid by using the composition and a method of producing a labeled nucleic acid by using the composition.

DETAILED DESCRIPTION

Figure 1:
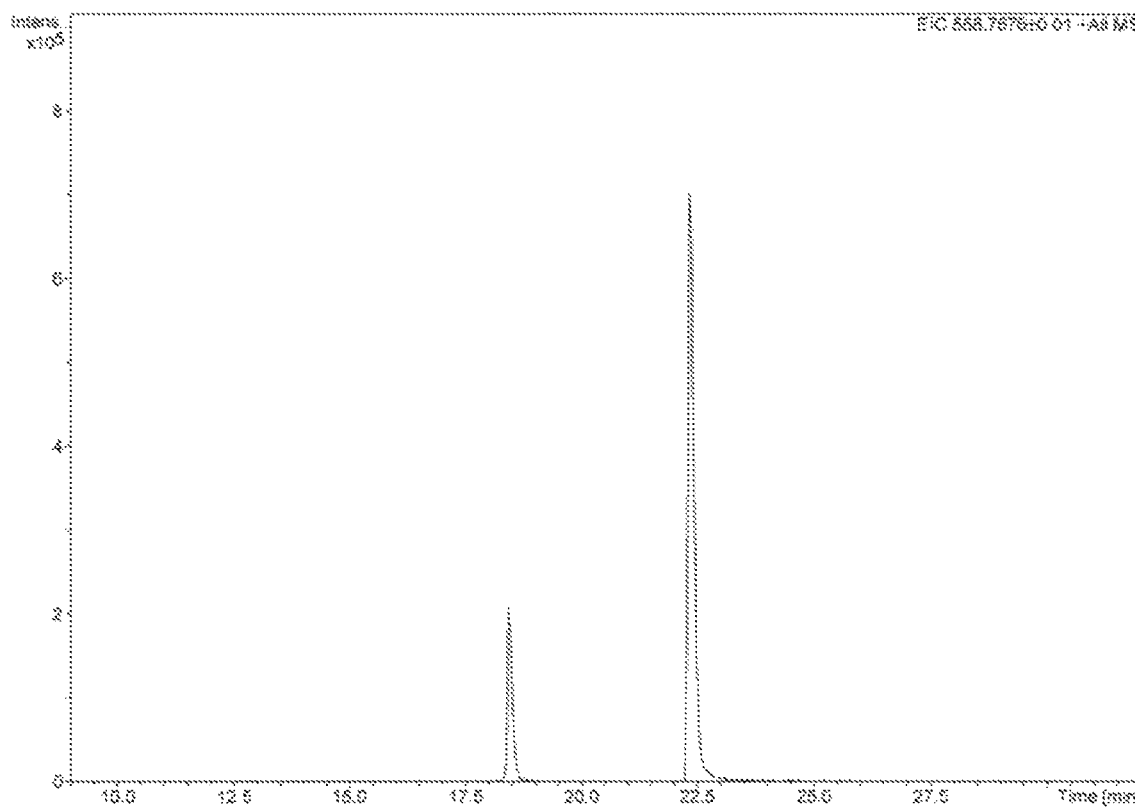
FIG. 1 shows an extracted ion chromatogram on the first peptide fragment obtained by an LC-MS/MS analysis of the composition C2 in Comparative Example 2.

Our compositions and methods will be described in detail below. It is possible to combine two or more of the configurations described below. This disclosure also encompasses such combinations. The expression "numerical value M to numerical value N" as used herein means a range of numerical value M or more and numerical value N or less.

Alkaline Phosphatase

Our compositions contain an alkaline phosphatase. The compositions may contain one alkaline phosphatase or may contain two or more alkaline phosphatases.

The alkaline phosphatase contained in the composition is not particularly limited as long as it has alkaline phosphatase activity. The alkaline phosphatase activity is activity that hydrolyzes a phosphoric monoester bond in alkalinity (pH 8 to 11, e.g., pH 8 to 10 or pH 9 to 11), and the reaction form is classified into EC3.1.3.1.

The structure of the alkaline phosphatase contained in the composition (e.g., primary structure, secondary structure, tertiary structure, quaternary structure and the like) is not particularly limited. For example, the alkaline phosphatase may have a sugar chain or may not have a sugar chain. The alkaline phosphatase may be any isozyme that can exist based on differences in the structure of a protein molecule (e.g., amino acid sequence of a protein molecule), glycosylation and the like. The alkaline phosphatase may be a monomer that is formed from one subunit or may be an oligomer that is formed from two or more subunits (e.g., dimer, tetramer and the like). The oligomer may be a homooligomer or may be a heterooligomer.

The animal from which the alkaline phosphatase contained in the composition is derived is not particularly limited. Examples of the animal from which the alkaline phosphatase is derived include a bovine, a shrimp, a microorganism into which a gene encoding an alkaline phosphatase has been introduced, and the like. Since a bovine-derived alkaline phosphatase has high alkaline phosphatase activity, the animal from which the alkaline phosphatase is derived is preferably a bovine. When the alkaline phosphatase is derived from a bovine, the organ from which the alkaline phosphatase is derived is preferably small intestine or large intestine.

The alkaline phosphatase contained in the composition may be wild-type or may be mutated. The mutated alkaline phosphatase contains, for example, a protein molecule consisting of an amino acid sequence obtained by introducing deletion, substitution, insertion or addition of one or more amino acids to an amino acid sequence of a protein molecule of a wild-type alkaline phosphatase. The amino acid sequence of the protein molecule of the mutated alkaline phosphatase has preferably 70% or more, more preferably 75% or more, still more preferably 80% or more, yet more preferably 85% or more, further preferably 90% or more, and still further preferably 95% or more sequence identity to the amino acid sequence of the protein molecule of the wild-type alkaline phosphatase.

Preferably, the alkaline phosphatase is selected from (a) and (b):
(a) an alkaline phosphatase containing a protein molecule consisting of the amino acid sequence set forth in SEQ ID NO: 10; and
(b) an alkaline phosphatase containing a protein molecule consisting of an amino acid sequence that has 70% or more sequence identity to the amino acid sequence set forth in SEQ ID NO: 10 and contains positions 78 to 90 (corresponding to the fourth peptide fragment), positions 177 to 187 (corresponding to the first peptide fragment), positions 469 to 477 (corresponding to the second peptide fragment), positions 516 to 528 (corresponding to the fifth peptide fragment) and positions 534 to 551 (corresponding to the third peptide fragment) of the amino acid sequence set forth in SEQ ID NO: 10. In this example, the composition may contain one alkaline phosphatase selected from (a) and (b), or may contain two or more alkaline phosphatases selected from (a) and (b). The alkaline phosphatase (b) contains positions 534 to 545 (corresponding to the sixth peptide fragment) of the amino acid sequence set forth in SEQ ID NO: 10.

The amino acid sequence of the protein molecule of the alkaline phosphatase (a) (i.e., the amino acid sequence set forth in SEQ ID NO: 10) corresponds to an amino acid sequence of a protein molecule of a bovine-derived alkaline phosphatase. Therefore, a bovine-derived alkaline phosphatase falls within the alkaline phosphatase (a).

The amino acid sequence of the protein molecule of the alkaline phosphatase (b) has preferably 70% or more, more preferably 75% or more, still more preferably 80% or more, yet more preferably 85% or more, further preferably 90% or more, and still further preferably 95% or more sequence identity to the amino acid sequence set forth in SEQ ID NO: 10.

Both of a wild-type alkaline phosphatase (e.g., an alkaline phosphatase derived from an animal other than a bovine, a bovine-derived alkaline phosphatase having a polymorphism or the like) and a mutated alkaline phosphatase fall within the alkaline phosphatase (b). The position(s) at which one or more amino acids are deleted, substituted, inserted or added in the amino acid sequence set forth in SEQ ID NO: 10 is/are a position(s) other than positions 78 to 90, positions 177 to 187, positions 469 to 477, positions 516 to 528 and positions 534 to 551 of the amino acid sequence set forth in SEQ ID NO: 10.

The alkaline phosphatases (a) and (b) can generate the first to sixth peptide fragments and the like by decomposition of the alkaline phosphatases.

Preferably, the amino acid sequence of the protein molecule of the alkaline phosphatase (b) contains one or two or more selected from positions 91 to 109, positions 93 to 105 and positions 529 to 531 of the amino acid sequence set forth in SEQ ID NO: 10. In this example, the alkaline phosphatase (b) can generate one or two or more of the seventh to ninth peptide fragments by decomposition of the alkaline phosphatase. In this example, the alkaline phosphatase (b) contains one or two or more selected from positions 86 to 109 (corresponding to the seventh peptide fragment), positions 93 to 105 (corresponding to the ninth peptide fragment) and positions 516 to 531 (corresponding to the eighth peptide fragment) of the amino acid sequence set forth in SEQ ID NO: 10.

Preferably, the alkaline phosphatase (b) contains positions 91 to 109 and positions 529 to 531 of the amino acid sequence set forth in SEQ ID NO: 10. In this example, the alkaline phosphatase (b) can generate the seventh to ninth peptide fragments by decomposition of the alkaline phosphatase. In this example, the alkaline phosphatase (b) contains positions 86 to 109 (corresponding to the seventh peptide fragment), positions 93 to 105 (corresponding to the ninth peptide fragment) and positions 516 to 531 (corresponding to the eighth peptide fragment) of the amino acid sequence set forth in SEQ ID NO: 10.

Peptide Fragment

The composition contains the first peptide fragment consisting of the amino acid sequence set forth in SEQ ID NO: 1, the second peptide fragment consisting of the amino acid sequence set forth in SEQ ID NO: 2, the third peptide fragment consisting of the amino acid sequence set forth in SEQ ID NO: 3, the fourth peptide fragment consisting of the amino acid sequence set forth in SEQ ID NO: 4, the fifth peptide fragment consisting of the amino acid sequence set forth in SEQ ID NO: 5 and the sixth peptide fragment consisting of the amino acid sequence set forth in SEQ ID NO: 6.

The amino acid sequence set forth in SEQ ID NO: 1 (DRQVPDSAGTA) corresponds to positions 177 to 187 of the amino acid sequence set forth in SEQ ID NO: 10. The amino acid sequence set forth in SEQ ID NO: 2 (APGKALDSK) corresponds to positions 469 to 477 of the amino acid sequence set forth in SEQ ID NO: 10. The amino acid sequence set forth in SEQ ID NO: 3 (GPQAHLVHGVQEETFVAH) corresponds to positions 534 to 551 of the amino acid sequence set forth in SEQ ID NO: 10. The amino acid sequence set forth in SEQ ID NO: 4 (EGVSLEKREAEAE) corresponds to positions 78 to 90 of the amino acid sequence set forth in SEQ ID NO: 10. The amino acid sequence set forth in SEQ ID NO: 5 (VPLASETHGGEDV) corresponds to positions 516 to 528 of the amino acid sequence set forth in SEQ ID NO: 10. The amino acid sequence set forth in SEQ ID NO: 6 (GPQAHLVHGVQE) corresponds to positions 534 to 545 of the amino acid sequence set forth in SEQ ID NO: 10.

The amino acid sequences of the first to sixth peptide fragments correspond to positions 177 to 187, positions 469 to 477, positions 534 to 551, positions 78 to 90, positions 516 to 528 and positions 534 to 545 of the amino acid sequence set forth in SEQ ID NO: 10, respectively. In other words, the first to sixth peptide fragments can be generated by decomposition of positions 177 to 187, positions 469 to 477, positions 534 to 551, positions 78 to 90, positions 516 to 528 and positions 534 to 545 of the amino acid sequence set forth in SEQ ID NO: 10, respectively. This does not mean that the alkaline phosphatase contained in the composition is required to contain positions 177 to 187, positions 469 to 477, positions 534 to 551, positions 78 to 90, positions 516 to 528 and positions 534 to 545 of the amino acid sequence set forth in SEQ ID NO: 10. The alkaline phosphatase contained in the composition may not contain one or two or more of positions 177 to 187, positions 469 to 477, positions 534 to 551, positions 78 to 90, positions 516 to 528 and positions 534 to 545 of the amino acid sequence set forth in SEQ ID NO: 10. However, the alkaline phosphatase contained in the composition preferably contains positions 177 to 187, positions 469 to 477, positions 534 to 551, positions 78 to 90, positions 516 to 528 and positions 534 to 545 of the amino acid sequence set forth in SEQ ID NO: 10.

The first to sixth peptide fragments may be those generated by decomposition of an alkaline phosphatase not contained in the composition, but are usually those generated by decomposition of an alkaline phosphatase contained in the composition. Therefore, preferably, the alkaline phosphatase contained in the composition is an alkaline phosphatase that can generate the first to sixth peptide fragments. Preferably, the alkaline phosphatase that can generate the first to sixth peptide fragments is selected from the alkaline phosphatases (a) and (b). In this example, the composition contains one or two or more alkaline phosphatases selected from the alkaline phosphatases (a) and (b).

Preferably, the composition further contains one or two or more peptide fragments selected from the group consisting of the seventh peptide fragment consisting of the amino acid sequence set forth in SEQ ID NO: 7, the eighth peptide fragment consisting of the amino acid sequence set forth in SEQ ID NO: 8 and the ninth peptide fragment consisting of the amino acid sequence set forth in SEQ ID NO: 9.

Preferably, the composition contains all of the seventh to ninth peptide fragments.

The amino acid sequence set forth in SEQ ID NO: 7 (EAEAEFLIPAEEENPAFWNRQAAQ) corresponds to positions 86 to 109 of the amino acid sequence set forth in SEQ ID NO: 10. The amino acid sequence set forth in SEQ ID NO: 8 (VPLASETHGGEDVAVF) corresponds to positions 516 to 531 of the amino acid sequence set forth in SEQ ID NO: 10. The amino acid sequence set forth in SEQ ID NO: 9 (IPAEEENPAFWNR) corresponds to positions 93 to 105 of the amino acid sequence set forth in SEQ ID NO: 10.

The amino acid sequences of the seventh to ninth peptide fragments correspond to positions 86 to 109, positions 516 to 531 and positions 93 to 105 of the amino acid sequence set forth in SEQ ID NO: 10, respectively. In other words, the seventh to ninth peptide fragments can be generated by decomposition of positions 86 to 109, positions 516 to 531 and positions 93 to 105 of the amino acid sequence set forth in SEQ ID NO: 10, respectively. This does not mean that the alkaline phosphatase contained in the composition is required to contain positions 86 to 109, positions 516 to 531 and positions 93 to 105 of the amino acid sequence set forth in SEQ ID NO: 10. The alkaline phosphatase contained in the composition may not contain one or two or more of positions 86 to 109, positions 516 to 531 and positions 93 to 105 of the amino acid sequence set forth in SEQ ID NO: 10. However, the alkaline phosphatase contained in the composition preferably contains positions 86 to 109, positions 516 to 531 and positions 93 to 105 of the amino acid sequence set forth in SEQ ID NO: 10.

The seventh to ninth peptide fragments may be those generated by decomposition of an alkaline phosphatase not contained in the composition, but are usually those generated by decomposition of an alkaline phosphatase contained in the composition. Therefore, preferably, the alkaline phosphatase contained in the composition is an alkaline phosphatase that can generate the seventh to ninth peptide fragments. Preferably, the alkaline phosphatase that can generate the seventh to ninth peptide fragments is selected from the alkaline phosphatases (a) and (b). In this example, the composition contains one or two or more alkaline phosphatases selected from the alkaline phosphatases (a) and (b).

The composition may contain a peptide fragment other than the first to ninth peptide fragments. The peptide fragment other than the first to ninth peptide fragments is, for example, one generated by decomposition of an alkaline phosphatase contained in the composition.

Content Ratios

In the composition, the content ratios of the first to sixth peptide fragments to the alkaline phosphatase satisfy formulas (1) to (6), respectively:

$$(X_1/Y) \times 100 \leq 0.6000 \quad (1);$$

$$(X_2/Y) \times 100 \leq 0.1800 \quad (2);$$

$$(X_3/Y) \times 100 \leq 0.2000 \quad (3);$$

$$(X_4/Y) \times 100 \leq 0.8000 \quad (4);$$

$$(X_5/Y) \times 100 \leq 1.6000 \quad (5); \text{ and}$$

$$(X_6/Y) \times 100 \leq 0.3500 \quad (6).$$

In formulas (1) to (6), $X_1$ to $X_6$ represent peak area values of the first to sixth peptide fragments calculated by an automatic integration method from an extracted ion chromatogram obtained by an LC-MS/MS analysis of the composition, respectively, and Y represents a peak area value of the alkaline phosphatase calculated by an automatic integration method from a chromatogram obtained by an LC-UV analysis of the composition.

In an example in which the composition further contains the seventh peptide fragment, the content ratio of the seventh peptide fragment to the alkaline phosphatase preferably satisfies formula (7):

$$(X_7/Y) \times 100 \leq 1.0000 \quad (7).$$

In formula (7), $X_7$ represents a peak area value of the seventh peptide fragment calculated by an automatic integration method from an extracted ion chromatogram obtained by an LC-MS/MS analysis of the composition, and Y is the same as defined above.

In an example in which the composition further contains the eighth peptide fragment, the content ratio of the eighth peptide fragment to the alkaline phosphatase preferably satisfies formula (8):

$$(X_8/Y) \times 100 \leq 1.0000 \quad (8).$$

In formula (8), $X_8$ represents a peak area value of the eighth peptide fragment calculated by an automatic integration method from an extracted ion chromatogram obtained by an LC-MS/MS analysis of the composition, and Y is the same as defined above.

In an example in which the composition further contains the ninth peptide fragment, the content ratio of the ninth peptide fragment to the alkaline phosphatase preferably satisfies formula (9):

$$(X_9/Y) \times 100 \leq 2.3000 \quad (9).$$

In formula (9), $X_9$ represents a peak area value of the ninth peptide fragment calculated by an automatic integration method from an extracted ion chromatogram obtained by an LC-MS/MS analysis of the composition, and Y is the same as defined above.

The LC-MS/MS analysis and the LC-UV analysis are performed by using a sample in which the content ratio of the first peptide fragment to the alkaline phosphatase (($X_1$/Y)×100), the content ratio of the second peptide fragment to the alkaline phosphatase (($X_2$/Y)×100), the content ratio of the third peptide fragment to the alkaline phosphatase (($X_3$/Y)×100), the content ratio of the fourth peptide fragment to the alkaline phosphatase (($X_4$/Y)×100), the content ratio of the fifth peptide fragment to the alkaline phosphatase (($X_5$/Y)×100) and the content ratio of the sixth peptide fragment to the alkaline phosphatase (($X_6$/Y)×100) are the same as those of the composition, respectively. The LC-MS/MS analysis and the LC-UV analysis can be performed, for example, by using an aqueous solution prepared from the composition and with an alkaline phosphatase concentration of 10% by weight.

The LC-MS/MS analysis is one of the hyphenated methods. The hyphenated method is a method of analyzing by connecting a chromatograph such as a gas chromatograph and a liquid chromatograph to a mass spectrometer. The LC-MS/MS analysis is a method of analyzing by connecting a liquid chromatograph (LC) to a tandem mass spectrometer (MS/MS). In the LC-MS/MS analysis, analyte components separated by the liquid chromatograph are ionized, the ions thus produced are separated by the tandem mass spectrometer, and specific mass ions are fragmented and detected.

In the hyphenated method, an extracted ion chromatogram is a chromatogram expressed as a function of time obtained by measuring a mass spectrum at a certain time interval and storing it in a computer, followed by reading a relative intensity at a specific (not necessarily one type) m/z value. The m/z value of an ion used to detect a peak of each of the first to ninth peptide fragments is preferably 50 to 2,200, more preferably 200 to 1,500, and still more preferably 300 to 1,200. An extracted ion chromatogram of each of the first to ninth peptide fragments can be created based on the m/z value. The m/z value of the first peptide fragment is 558.7676, the m/z value of the second peptide fragment is 443.7533, the m/z value of the third peptide fragment is 652.6623, the m/z value of the fourth peptide fragment is 723.8572, the m/z value of the fifth peptide fragment is 655.8148, the m/z value of the sixth peptide fragment is 636.3282, the m/z value of the seventh peptide fragment is 920.7682, the m/z value of the eighth peptide fragment is 814.4018, and the m/z value of the ninth peptide fragment is 786.8757. Regarding a peptide fragment with an m/z value not being specified, after confirmation by an amino acid sequence analysis of a predetermined peptide fragment showing a certain peak, it is possible to create an extracted ion chromatogram of the peptide fragment based on the m/z value of the peak.

The LC-UV analysis is a method of analyzing by connecting a liquid chromatograph (LC) to an ultraviolet detector (UV detector). In the LC-UV analysis, an alkaline phosphatase is detected as a component having absorption at 214 nm.

Conditions of the LC-MS/MS analysis are as follows.
Conditions of LC-MS/MS Analysis
Apparatus Configuration
    Mass spectrometer: maXis impact (manufactured by Bruker Daltnics, Inc.) Conditions of Mass Spectrometry
    Ionization method: ESI
    Measured ion: cation
    Capillary voltage: 4,500 V
    Nebulizer: 2.0 bar
    Dry gas: 8.0 L/min
    Detector voltage: 1,823 V
    Measuring span (MS): m/z 50 to 2,200
MS/MS Conditions
    Measuring span (MS): m/z 50 to 2,200
    Collision gas: nitrogen
Conditions of LC-UV Analysis
Apparatus Configuration
    Liquid chromatograph: LC-30A system (manufactured by Shimadzu Corporation)
    Detector: UV-Vis (190 to 900 nm, manufactured by Shimadzu Corporation)
Conditions of Liquid Chromatography
    Column: Acquity BEH C18 1.7 μm (manufactured by Waters Corporation)
    Column size: 2.1 mm×100 mm
    Column temperature: 50° C.
    Mobile phase flow rate: 0.2 mL/min
    Mobile phase A: mixed solution of water/formic acid (1000:1)
    Mobile phase B: mixed solution of acetonitrile/water/formic acid (900:100:1)
    Injection volume: 20 μL
    Gradient program:

TABLE 1

| Times (min) | Mobile phase A (vol %) | Mobile phase B (vol %) |
|---|---|---|
| 0 | 100 | 0 |
| 10 | 100 | 0 |
| 40 | 35 | 65 |
| 40.1 | 0 | 100 |
| 50 | 0 | 100 |
| 50.1 | 100 | 0 |
| 60 | 100 | 0 |

The value of $(X_1/Y) \times 100$ is not particularly limited as long as it is 0.6000 or less, and the smaller the value is, the more preferable it is. The value of $(X_1/Y) \times 100$ is preferably 0.5000 or less, more preferably 0.3000 or less, and still more preferably 0.2000 or less. The lower limit of $(X_1/Y) \times 100$ is a detection limit. In terms of obtaining an effect that matches an effort to decrease the value of $(X_1/Y) \times 100$ (e.g., removal and separation of the first peptide fragment by purification), the value of $(X_1/Y) \times 100$ is preferably 0.0500 or more, more preferably 0.0600 or more, and still more preferably 0.0700 or more.

The value of $(X_2/Y) \times 100$ is not particularly limited as long as it is 0.1800 or less, and the smaller the value is, the more preferable it is. The value of $(X_2/Y) \times 100$ is preferably 0.1500 or less, more preferably 0.1200 or less, and still more preferably 0.1000 or less. The lower limit of $(X_2/Y) \times 100$ is a detection limit. In terms of obtaining an effect that matches an effort to decrease the value of $(X_2/Y) \times 100$ (e.g., removal and separation of the second peptide fragment by purification), the value of $(X_2/Y) \times 100$ is preferably 0.0500 or more, more preferably 0.0600 or more, and still more preferably 0.0700 or more.

The value of $(X_3/Y) \times 100$ is not particularly limited as long as it is 0.2000 or less, and the smaller the value is, the more preferable it is. The value of $(X_3/Y) \times 100$ is preferably 0.1800 or less, more preferably 0.1700 or less, and still more preferably 0.1500 or less. The lower limit of $(X_3/Y) \times 100$ is a detection limit. In terms of obtaining an effect that matches an effort to decrease the value of $(X_3/Y) \times 100$ (e.g., removal and separation of the third peptide fragment by purification), the value of $(X_3/Y) \times 100$ is preferably 0.0500 or more, more preferably 0.0600 or more, and still more preferably 0.0700 or more.

The value of $(X_4/Y) \times 100$ is not particularly limited as long as it is 0.8000 or less, and the smaller the value is, the more preferable it is. The value of $(X_4/Y) \times 100$ is preferably 0.7000 or less, more preferably 0.6000 or less, and still more preferably 0.5000 or less. The lower limit of $(X_4/Y) \times 100$ is a detection limit. In terms of obtaining an effect that matches an effort to decrease the value of $(X_4/Y) \times 100$ (e.g., removal and separation of the fourth peptide fragment by purification), the value of $(X_4/Y) \times 100$ is preferably 0.0500 or more, more preferably 0.0600 or more, and still more preferably 0.0700 or more.

The value of $(X_5/Y) \times 100$ is not particularly limited as long as it is 1.6000 or less, and the smaller the value is, the more preferable it is. The value of $(X_5/Y) \times 100$ is preferably 1.5000 or less, more preferably 1.2000 or less, and still more preferably 1.0000 or less. The lower limit of $(X_5/Y) \times 100$ is a detection limit. In terms of obtaining an effect that matches an effort to decrease the value of $(X_5/Y) \times 100$ (e.g., removal and separation of the fifth peptide fragment by purification), the value of $(X_5/Y) \times 100$ is preferably 0.0500 or more, more preferably 0.0600 or more, and still more preferably 0.0700 or more.

The value of $(X_6/Y) \times 100$ is not particularly limited as long as it is 0.3500 or less, and the smaller the value is, the more preferable it is. The value of $(X_6/Y) \times 100$ is preferably 0.3200 or less, more preferably 0.3000 or less, and still more preferably 0.2800 or less. The lower limit of $(X_6/Y) \times 100$ is a detection limit. In terms of obtaining an effect that matches an effort to decrease the value of $(X_6/Y) \times 100$ (e.g., removal and separation of the sixth peptide fragment by purification), the value of $(X_6/Y) \times 100$ is preferably 0.0800 or more, more preferably 0.1000 or more, and still more preferably 0.1500 or more.

The value of $(X_7/Y) \times 100$ is not particularly limited as long as it is 1.0000 or less, and the smaller the value is, the more preferable it is. The value of $(X_7/Y) \times 100$ is preferably 0.9000 or less, more preferably 0.8000 or less, and still more preferably 0.7000 or less. The lower limit of $(X_7/Y) \times 100$ is a detection limit. In terms of obtaining an effect that matches an effort to decrease the value of $(X_7/Y) \times 100$ (e.g., removal and separation of the seventh peptide fragment by purification), the value of $(X_7/Y) \times 100$ is preferably 0.0500 or more, more preferably 0.0600 or more, and still more preferably 0.0700 or more.

The value of $(X_8/Y) \times 100$ is not particularly limited as long as it is 1.0000 or less, and the smaller the value is, the more preferable it is. The value of $(X_8/Y) \times 100$ is preferably 0.9000 or less, more preferably 0.8000 or less, and still more preferably 0.7000 or less. The lower limit of $(X_8/Y) \times 100$ is a detection limit. In terms of obtaining an effect that matches an effort to decrease the value of $(X_8/Y) \times 100$ (e.g., removal and separation of the eighth peptide fragment by purification), the value of $(X_8/Y) \times 100$ is preferably 0.0500 or more, more preferably 0.0600 or more, and still more preferably 0.0700 or more.

The value of $(X_9/Y) \times 100$ is not particularly limited as long as it is 2.3000 or less, and the smaller the value is, the more preferable it is. The value of $(X_9/Y) \times 100$ is preferably 2.0000 or less, more preferably 1.5000 or less, and still more preferably 1.0000 or less. The lower limit of $(X_9/Y) \times 100$ is a detection limit. In terms of obtaining an effect that matches an effort to decrease the value of $(X_9/Y) \times 100$ (e.g., removal and separation of the ninth peptide fragment by purification), the value of $(X_9/Y) \times 100$ is preferably 0.0500 or more, more preferably 0.0600 or more, and still more preferably 0.0700 or more.

The smaller the peak area value of the first peptide fragment, which is calculated by an automatic integration method from an extracted ion chromatogram obtained by an LC-MS/MS analysis performed by using an aqueous solution prepared from the composition and with an alkaline phosphatase concentration of 10% by weight, is, the more preferable it is. The peak area value of the first peptide fragment is preferably 1,500 or less, more preferably 1,200 or less, and still more preferably 1,000 or less. The lower limit of the peak area value of the first peptide fragment is a detection limit. In terms of obtaining an effect that matches an effort to decrease the peak area value of the first peptide fragment (e.g., removal and separation of the first peptide fragment by purification), the peak area value of the first peptide fragment is preferably 100 or more, more preferably 150 or more, and still more preferably 200 or more.

The smaller the peak area value of the second peptide fragment, which is calculated by an automatic integration method from an extracted ion chromatogram obtained by an LC-MS/MS analysis performed by using an aqueous solution prepared from the composition and with an alkaline phosphatase concentration of 10% by weight, is, the more preferable it is. The peak area value of the second peptide fragment is preferably 400 or less, more preferably 380 or less, and still more preferably 350 or less. The lower limit of the peak area value of the second peptide fragment is a detection limit. In terms of obtaining an effect that matches an effort to decrease the peak area value of the second peptide fragment (e.g., removal and separation of the second peptide fragment by purification), the peak area value of the second peptide fragment is preferably 100 or more, more preferably 130 or more, and still more preferably 150 or more.

The smaller the peak area value of the third peptide fragment, which is calculated by an automatic integration method from an extracted ion chromatogram obtained by an LC-MS/MS analysis performed by using an aqueous solution prepared from the composition and with an alkaline phosphatase concentration of 10% by weight, is, the more preferable it is. The peak area value of the third peptide fragment is preferably 500 or less, more preferably 450 or less, and still more preferably 400 or less. The lower limit of the peak area value of the third peptide fragment is a detection limit. In terms of obtaining an effect that matches an effort to decrease the peak area value of the third peptide fragment (e.g., removal and separation of the third peptide fragment by purification), the peak area value of the third peptide fragment is preferably 100 or more, more preferably 150 or more, and still more preferably 200 or more.

The smaller the peak area value of the fourth peptide fragment, which is calculated by an automatic integration method from an extracted ion chromatogram obtained by an LC-MS/MS analysis performed by using an aqueous solution prepared from the composition and with an alkaline phosphatase concentration of 10% by weight, is, the more preferable it is. The peak area value of the fourth peptide fragment is preferably 2,000 or less, more preferably 1,800 or less, and still more preferably 1,500 or less. The lower limit of the peak area value of the fourth peptide fragment is a detection limit. In terms of obtaining an effect that matches an effort to decrease the peak area value of the fourth peptide fragment (e.g., removal and separation of the fourth peptide fragment by purification), the peak area value of the fourth peptide fragment is preferably 100 or more, more preferably 150 or more, and still more preferably 200 or more.

The smaller the peak area value of the fifth peptide fragment, which is calculated by an automatic integration method from an extracted ion chromatogram obtained by an LC-MS/MS analysis performed by using an aqueous solution prepared from the composition and with an alkaline phosphatase concentration of 10% by weight, is, the more preferable it is. The peak area value of the fifth peptide fragment is preferably 4,500 or less, more preferably 3,000 or less, and still more preferably 2,500 or less. The lower limit of the peak area value of the fifth peptide fragment is a detection limit. In terms of obtaining an effect that matches an effort to decrease the peak area value of the fifth peptide fragment (e.g., removal and separation of the fifth peptide fragment by purification), the peak area value of the fifth peptide fragment is preferably 100 or more, more preferably 150 or more, and still more preferably 200 or more.

The smaller the peak area value of the sixth peptide fragment, which is calculated by an automatic integration method from an extracted ion chromatogram obtained by an LC-MS/MS analysis performed by using an aqueous solution prepared from the composition and with an alkaline phosphatase concentration of 10% by weight, is, the more preferable it is. The peak area value of the sixth peptide fragment is preferably 1,000 or less, more preferably 900 or less, and still more preferably 800 or less. The lower limit of the peak area value of the sixth peptide fragment is a detection limit. In terms of obtaining an effect that matches an effort to decrease the peak area value of the sixth peptide fragment (e.g., removal and separation of the sixth peptide fragment by purification), the peak area value of the sixth peptide fragment is preferably 100 or more, more preferably 150 or more, and still more preferably 200 or more.

The smaller the peak area value of the seventh peptide fragment, which is calculated by an automatic integration method from an extracted ion chromatogram obtained by an LC-MS/MS analysis performed by using an aqueous solution prepared from the composition and with an alkaline phosphatase concentration of 10% by weight, is, the more preferable it is. The peak area value of the seventh peptide fragment is preferably 3,000 or less, more preferably 2,500 or less, and still more preferably 2,000 or less. The lower limit of the peak area value of the seventh peptide fragment is a detection limit. In terms of obtaining an effect that matches an effort to decrease the peak area value of the seventh peptide fragment (e.g., removal and separation of the seventh peptide fragment by purification), the peak area value of the seventh peptide fragment is preferably 100 or more, more preferably 150 or more, and still more preferably 200 or more.

The smaller the peak area value of the eighth peptide fragment, which is calculated by an automatic integration method from an extracted ion chromatogram obtained by an LC-MS/MS analysis performed by using an aqueous solution prepared from the composition and with an alkaline phosphatase concentration of 10% by weight, is, the more preferable it is. The peak area value of the eighth peptide fragment is preferably 3,000 or less, more preferably 2,500 or less, and still more preferably 2,000 or less. The lower limit of the peak area value of the eighth peptide fragment is a detection limit. In terms of obtaining an effect that matches an effort to decrease the peak area value of the eighth peptide fragment (e.g., removal and separation of the eighth peptide fragment by purification), the peak area value of the eighth peptide fragment is preferably 100 or more, more preferably 150 or more, and still more preferably 200 or more.

The smaller the peak area value of the ninth peptide fragment, which is calculated by an automatic integration method from an extracted ion chromatogram obtained by an LC-MS/MS analysis performed by using an aqueous solution prepared from the composition and with an alkaline phosphatase concentration of 10% by weight, is, the more preferable it is. The peak area value of the ninth peptide fragment is preferably 6,000 or less, more preferably 3,000 or less, and still more preferably 1,000 or less. The lower limit of the peak area value of the ninth peptide fragment is a detection limit. In terms of obtaining an effect that matches an effort to decrease the peak area value of the ninth peptide fragment (e.g., removal and separation of the ninth peptide fragment by purification), the peak area value of the ninth peptide fragment is preferably 100 or more, more preferably 150 or more, and still more preferably 200 or more.

The peak area value of an alkaline phosphatase, which is calculated by an automatic integration method from a chromatogram obtained by an LC-UV analysis performed by using an aqueous solution prepared from the composition and with an alkaline phosphatase concentration of 10% by weight, is preferably 200,000 or more, more preferably 220,000 or more, and still more preferably 240,000 or more. The upper limit of the peak area value of an alkaline phosphatase is not particularly limited. The peak area value of an alkaline phosphatase is preferably 500,000 or less, more preferably 400,000 or less, and still more preferably 350,000 or less.

Alkaline Phosphatase Specific Activity

The composition preferably has an alkaline phosphatase specific activity of 2,000 U/mg or more. The alkaline phosphatase specific activity of the composition is more preferably 2,500 U/mg or more, and still more preferably 3,000 U/mg or more. The alkaline phosphatase specific activity of the composition is measured as follows. By measuring the absorbance at 405 nm derived from p-nitrophenol produced by adding an alkaline phosphatase to an aqueous solution of p-nitrophenylphosphate, it is possible to calculate the specific activity of the alkaline phosphatase.

Other Components

The composition can contain one or two or more other components. Examples of the other components include aqueous vehicles such as water, metal salts such as a magnesium salt and a sodium salt, surfactants, organic acids, glycerin and the like.

The composition can be used for various applications requiring an alkaline phosphatase activity, and can contain one or two or more other components selected according to the applications.

In one example, the composition contains a protein such as an antigen and an antibody. In this example, the composition can be used to label a protein such as an antigen and an antibody with the alkaline phosphatase. In other words, in one example, the composition is a composition used to label a protein with the alkaline phosphatase. Labeling of a protein with the alkaline phosphatase can be performed by reacting a succinimide ester of the alkaline phosphatase, which is obtained by esterifying a carboxyl group of the alkaline phosphatase with succinimide, with an amino group of the protein.

In one example, the composition contains a substrate for the alkaline phosphatase. In this example, the composition can be used to dephosphorylate a substrate for the alkaline phosphatase. In other words, in one example, the composition is a composition used to dephosphorylate a substrate for the alkaline phosphatase. The substrate for the alkaline phosphatase is not particularly limited as long as the substrate is a compound having a phosphoric monoester bond. Examples of the substrate for the alkaline phosphatase include a nucleic acid, a phospholipid, pyrophosphoric acid and the like. When the substrate for the alkaline phosphatase is treated with the composition, the phosphoric monoester bond of the substrate for the alkaline phosphatase is hydrolyzed by the alkaline phosphatase, resulting in dephosphorylation of the substrate for the alkaline phosphatase.

Preferably, the composition contains a nucleic acid. In this example, the composition can be used to dephosphorylate a nucleic acid. In other words, preferably, the composition is used to dephosphorylate a nucleic acid. The first to sixth peptide fragments coexisting in the alkaline phosphatase have a possibility of adversely influencing when the nucleic acid is dephosphorylated by the alkaline phosphatase. In this regard, in the composition, the content ratios of the first to sixth peptide fragments to the alkaline phosphatase satisfy formulas (1) to (6), respectively. In other words, in the composition, the relative contents of the first to sixth peptide fragments have been reduced. Therefore, by using the composition, it is possible to reduce the adverse influence of the first to sixth peptide fragments that can occur when the nucleic acid is dephosphorylated by the alkaline phosphatase, thus enabling improvement in the dephosphorylation efficiency of the nucleic acid. By treating the nucleic acid with the composition, the 5' end and/or the 3' end of the nucleic acid can be dephosphorylated. By dephosphorylating the 5' end and/or the 3' end of the nucleic acid, it is possible to improve the labeling efficiency when the 5' end and/or the 3' end of the nucleic acid is/are labeled with the labeling substance. Particularly, when $^{32}P$ is used as the labeling substance, this effect is remarkable. By dephosphorylating the 5' end and/or the 3' end of a vector used for DNA cloning, self-ligation of the vector can be prevented, thus enabling a reduction in the background of a transformed cell.

Examples of the nucleic acid include nucleic acids such as DNA, RNA, peptide nucleic acid (PNA) and locked nucleic acid (LNA) or a nucleic acid derivative. Examples of the nucleic acid derivative include a nucleic acid derivative containing a modified nucleotide (e.g., a nucleotide that has undergone reconstitution of a nucleotide or base containing a halogen group, an alkyl group such as a methyl group, an alkoxy group such as a methoxy group, a thio group and a carboxymethyl group, saturation of a double bond, deamination, substitution of an oxygen molecule with a sulfur molecule and the like). The nucleic acid may be single-stranded or double-stranded. Examples of the DNA include chromosomal DNA, viral DNA, DNA of a bacterium, a fungus, cDNA, fragments thereof and the like. Examples of the RNA include mRNA, rRNA, small RNA, fragments thereof and the like. The nucleic acid may be chemically synthesized DNA, RNA and the like. Specific examples of the nucleic acid include a gene of a pathogen, a virus or a part thereof, a causative gene for genetic disease or a part thereof and the like.

The nucleic acid can be prepared by an extraction by a conventional method from, for example, a biomaterial, a virus, a bacterium, a fungus, a food and drink and the like. Examples of the biomaterial include body fluids such as blood, serum, plasma, urine, stool, spinal fluid, saliva, swab and tissue fluid, a cell, a tissue and the like. The biomaterial may be animal-derived or plant-derived.

The amount of the nucleic acid contained in the composition can be appropriately adjusted according to the intended use of the composition (e.g., detection of the target nucleic acid) and the like. For example, when a certain nucleic acid (i.e., a target nucleic acid) among nucleic acids contained in the composition is intended to be detected, it is possible to amplify the target nucleic acid by performing a nucleic acid amplification method such as PCR by using the nucleic acids contained in the composition as a template. This enables improvement in the detection sensitivity of the target nucleic acid.

The length (number of bases) of the nucleic acid can be appropriately adjusted according to the intended use of the composition (e.g., detection of the target nucleic acid) and the like. For example, when the nucleic acid is intended to be detected, the length of the nucleic acid is usually 10 to 300 bases, preferably 10 to 100 bases, and more preferably 15 to 50 bases. The length of the nucleic acid can be appropriately adjusted by fragmentation treatment. The length of the nucleic acid is, for example, a length at which the nucleic acid can be hybridized with a probe. When the nucleic acid is long (e.g., 1,500 bases or more, particularly 4,000 bases or more), it is preferable to perform fragmentation treatment of the nucleic acid and to adjust the length of the nucleic acid to an appropriate length. When fragmentation treatment is performed, it is not necessarily that a specific nucleic acid fragment is selected from the generated nucleic acid fragments, and the fragmentation product can be used as it is.

Examples of a method of cleaving the nucleic acid for fragmentation include a method of cleaving by irradiation with ultrasonic waves, a method of cleaving with an enzyme, a method of cleaving with a restriction enzyme, a method using a nebulizer, a method of cleaving with an acid or an alkali and the like. In the method of cleaving with ultrasonic waves, by controlling the output intensity and the irradiation time of the ultrasonic waves with which the nucleic acid is irradiated, it is possible to cleavage the nucleic acid into a desired length.

Preferably, the composition contains a dephosphorylated nucleic acid. The descriptions on the nucleic acid are the same as mentioned above. The dephosphorylated nucleic acid has a 5' end and/or a 3' end, each of which has been dephosphorylated by the alkaline phosphatase. In this example, the composition can be used for preparing a labeled nucleic acid containing the dephosphorylated nucleic acid and a labeling substance bound to the dephosphorylated nucleic acid. In other words, preferably, the composition is used to prepare a labeled nucleic acid containing the dephosphorylated nucleic acid and a labeling substance bound to the dephosphorylated nucleic acid. The first to sixth peptide fragments coexisting in the alkaline phosphatase have a possibility of adversely influencing when the nucleic acid is dephosphorylated by the alkaline phosphatase and/or when the labeling substance is bound to the dephosphorylated nucleic acid. In this regard, in the composition, the content ratios of the first to sixth peptide fragments to the alkaline phosphatase satisfy formulas (1) to (6), respectively. In other words, in the composition, the relative contents of the first to sixth peptide fragments have been reduced. Therefore, by using the composition, it is possible to reduce the adverse influence of the first to sixth peptide fragments that can occur when the nucleic acid is dephosphorylated by the alkaline phosphatase and/or when the labeling substance is bound to the dephosphorylated nucleic acid, thus enabling improvement in the dephosphorylation efficiency of the nucleic acid and/or the labeling efficiency of the dephosphorylated nucleic acid.

Preferably, the composition contains a labeled nucleic acid containing a dephosphorylated nucleic acid and a labeling substance bound to the dephosphorylated nucleic acid. The descriptions on the nucleic acid are the same as mentioned above. The dephosphorylated nucleic acid has a 5' end and/or a 3' end, each of which has been dephosphorylated by the alkaline phosphatase. The labeling substance is bound to the 5' end and/or the 3' end of the dephosphorylated nucleic acid.

As the labeling substance, for example, a fluorescent dye, a fluorescent protein, a chemiluminescent body, a metal complex, a metal fine particle, biotin, a radioisotope and the like, can be used. The reaction conditions when the target nucleic acid is labeled can be appropriately adjusted according to the type of the labeling substance. When the labeling substance is a fluorescent dye, the fluorescent dye can be detected by using a fluorescence microscope, a fluorescence scanner and the like.

Examples of the fluorescent dye include organic fluorescent dyes such as a fluorescein-based dye, a rhodamine-based dye, an Alexa Fluor (manufactured by Invitrogen)-based dye, a BODIPY (manufactured by Invitrogen)-based dye, a cascade-based dye, a coumarin-based dye, an eosin-based dye, an NBD-based dye, a pyrene-based dye, a Texas Red-based dye and a cyanine-based dye.

Specific examples of the organic fluorescent dye include 5-carboxy-fluorescein, 6-carboxy-fluorescein, 5,6-dicarboxy-fluorescein, 6-carboxy-2',4,4',5',7,7'-hexachloro-fluorescein, 6-carboxy-2',4,7,7'-tetrachloro-fluorescein, 6-carboxy-4',5'-dichloro-2',7'-dimethoxy-fluorescein, naphthofluorescein, 5-carboxy-rhodamine, 6-carboxy-rhodamine, 5,6-dicarboxy-rhodamine, rhodamine 6G, tetramethylrhodamine, X-rhodamine, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (all of which are manufactured by Invitrogen), methoxycoumarin, eosin, NBD, pyrene, Cy5, Cy5.5, Cy7 and the like.

In the example in which the composition contains a labeled nucleic acid containing a dephosphorylated nucleic acid and a labeling substance bound to the dephosphorylated nucleic acid, the composition can be used as a nucleic acid sample to be subjected to a nucleic acid detection method. In other words, preferably, the composition is a nucleic acid sample to be subjected to the nucleic acid detection method. The labeled nucleic acid can contain a target nucleic acid to be detected and a nucleic acid other than the target nucleic acid. In the nucleic acid detection method, the target nucleic acid contained in the nucleic acid sample can be detected by using the labeling substance of the target nucleic acid as an index. The nucleic acid detection method is not particularly limited, and can be appropriately selected from known nucleic acid detection methods. The target nucleic acid can be detected, for example, by using the hybridization method. In one example of the hybridization method, the target nucleic acid can be detected by using a probe that can be hybridized with the target nucleic acid. In one example of the nucleic acid detection method using a probe, the probe is brought into contact with the nucleic acid sample containing the target nucleic acid to hybridize the probe with the target nucleic acid, and the target nucleic acid hybridized with the probe can be detected by using the labeling substance of the target nucleic acid as an index. When a nucleic acid other than the target nucleic acid is contained in the sample, it is preferable that, after the target nucleic acid is brought into contact with the probe, the nucleic acid that was not hybridized with the probe is removed by washing or the like.

The reaction conditions when the target nucleic acid is hybridized with the probe can be appropriately adjusted according to chain length of the target nucleic acid, the chain length of the probe and the like. The reaction time is usually 30 to 1,200 minutes, and preferably 60 to 360 minutes. The reaction temperature is usually 25 to 60° C., and preferably 30 to 40° C. The reaction is usually performed in an aqueous vehicle such as water.

The amount of the target nucleic acid or probe used is not particularly limited as long as the hybridization between the target nucleic acid and the probe can occur and the labeling substance bound to the target nucleic acid can be detected, and the amount can be appropriately adjusted according to the chain length of the target nucleic acid, the chain length of the probe, the type of the labeling substance and the like.

As the probe, for example, nucleic acids such as DNA, RNA, peptide nucleic acid (PNA) and locked nucleic acid (LNA) or a nucleic acid derivative can be used. Examples of the nucleic acid derivative include a nucleic acid derivative containing a modified nucleotide (e.g., a nucleotide that has undergone reconstitution of a nucleotide or base containing a halogen group, an alkyl group such as a methyl group, an alkoxy group such as a methoxy group, a thio group and a carboxymethyl group and the like, saturation of a double bond, deamination, substitution of an oxygen molecule with a sulfur molecule and the like).

The probe has a base sequence complementary to at least a part of the base sequence of the target nucleic acid, and can be hybridized with the target nucleic acid. When the target nucleic acid is double-stranded, the probe may be hybridized with a sense strand or may be hybridized with an antisense strand. The base sequence of the probe may be complementary to any part of the base sequence of the target nucleic acid, and is preferably complementary to a highly-specific part of the base sequence of the target nucleic acid. In other words, the base sequence of the probe is preferably complementary to a base sequence which other nucleic acids contained in the sample do not have, of the base sequence of the target nucleic acid.

Of the base sequence of the probe, the length (number of bases) of the part complementary to the base sequence of the target nucleic acid is not particularly limited, and is usually 10 to 150 bases, preferably 20 to 100 bases, and more preferably 20 to 70 bases. The probe may be composed of a base sequence complementary to the base sequence of the target nucleic acid, or may include a base sequence not complementary to the base sequence of the target nucleic acid. The full length (total number of bases) of the probe is usually 10 to 300 bases, preferably 20 to 200 bases, and more preferably 15 to 100 bases.

The probe may be any of a commercially available product, a synthetic product, a prepared product from a living body and the like. A nucleic acid having a length of up to 200 bases, which is referred to as an oligonucleic acid, can be easily artificially synthesized with a synthesizer.

The probe is preferably fixed to a support. In other words, preferably, the nucleic acid detection method is a nucleic acid detection method using a nucleic acid microarray. The nucleic acid microarray has a support and a plurality of probes fixed to the surface of the support. In the nucleic acid detection method using a nucleic acid microarray, the labeled target nucleic acid is brought into contact with a nucleic acid microarray provided with a probe that can be hybridized with the target nucleic acid, and the target nucleic acid hybridized with the probe can be detected by using the labeling substance bound to the target nucleic acid as an index. When a nucleic acid other than the target nucleic acid is contained in the sample, it is preferable that, after the target nucleic acid is brought into contact with the nucleic acid microarray, the nucleic acid that has not been hybridized with the probe on the nucleic acid microarray is removed by washing or the like. By using a nucleic acid microarray provided with a plurality of probes, two or more target nucleic acids can be simultaneously detected.

The support is not particularly limited as long as it can fix the probe. Examples of the support include a slide, a membrane, a bead and the like. Examples of the material of the support include inorganic materials such as glass, ceramic and silicon, and polymers such as polyethylene terephthalate, cellulose acetate, polycarbonate, polystyrene, polymethyl methacrylate and silicone rubber and the like.

Fixation of the probe to the support can be performed in accordance with a conventional method. As a method of fixing the probe to the support, a method of synthesizing an oligonucleic acid on the top surface of the support, a method of adding dropwise an oligonucleic acid synthesized in advance to the top surface of the support to fix and the like are known. Examples of the former method include the method by U.S. Pat. No. 5,705,610 A, the method by U.S. Pat. No. 7,037,659 A and the like. In those methods, since an organic solvent is used during DNA synthesis reaction, the support is desirably a material that is resistance to an organic solvent. For example, it is possible to use a glass support having an irregular structure fabricated by using the method disclosed in JP H10-503841 A. Particularly, in the method by US '659, since the back of the support is irradiated with light to control DNA synthesis, the support is preferably a material having translucency. Examples of the latter method include the method by JP 3922454 B2, a method using a glass capillary and the like. As an example of the glass capillary, it is possible to use a self-made glass capillary, commercially available products such as a micropipette (manufactured by Micro Support Co., Ltd.; MP-005) and the like.

As a method detecting the target nucleic acid, the sandwich hybridization method can be used. In the sandwich hybridization method, a first probe (capture probe) fixed to the support and a second probe (detection probe) not fixed to the support are used. The capture probe and the detection probe each have a base sequence complementary to different parts of the target nucleic acid, and can be hybridized with different parts of the target nucleic acid. The target nucleic acid is hybridized with the detection probe and the capture probe, thus forming a complex. By detecting a labeling substance contained in this complex, the target nucleic acid can be detected.

The sequence identity between the base sequence of the detection probe and the base sequence of the capture probe is preferably low. The sequence identity is preferably 20% or less, and more preferably 10% or less. In this regard, the identity between two base sequences is a numerical value obtained by aligning two sequences (inserting a gap, if necessary) so that bases are matched as many as possible, and then by dividing the number of matched bases by total number of bases (the higher number of bases when the number of bases of two base sequences is different), and the identity can be easily calculated with commercially available software such as FASTA and BLAST (also provided via the internet).

The signal detected in the method of detecting the target nucleic acid (e.g., intensity of the detected labeling substance) is compared to a surrounding noise. Specifically, the signal value obtained from a position on the support at which a probe is fixed is compared with the signal value (noise value) obtained from a position of the support at which no probe is fixed, and a ratio of the former numerical value to the noise value is defined as an S/N ratio. The detection accuracy can be represented by the S/N ratio. In other words, the larger the S/N ratio is, the higher the detection accuracy is, and the smaller the S/N ratio is, the lower the detection accuracy is.

In the example in which the composition contains a labeled nucleic acid containing a dephosphorylated nucleic acid and a labeling substance bound to the dephosphorylated nucleic acid, by using the composition as a nucleic acid sample in the nucleic acid detection method, it is possible to improve the detection sensitivity of the target nucleic acid. This effect is remarkable in a nucleic acid detection method using an extremely small amount (preferably 5 to 1,000 µL, more preferably 5 to 500 µL) of a nucleic acid sample. In the nucleic acid detection method using an extremely small amount of a nucleic acid sample, the first to sixth peptide fragments contained in the nucleic acid sample have a possibility of adversely influencing the detection sensitivity. In this regard, in the composition, the content ratios of the first to sixth peptide fragments to the alkaline phosphatase satisfy formulas (1) to (6), respectively. In other words, in the composition, the relative contents of the first to sixth peptide fragments have been reduced. Therefore, in the nucleic acid detection method using an extremely small amount of a nucleic acid sample, by using the composition as the nucleic acid sample, it is possible to reduce the adverse influence of the first to sixth peptide fragments, thus enabling remarkable improvement in the detection sensitivity of the target nucleic acid.

Preferably, the nucleic acid detection method is a nucleic acid detection method using a nucleic acid microarray. In the nucleic acid detection method using a nucleic acid microarray, an extremely small amount (preferably 5 to 1,000 µL, more preferably 5 to 500 µL) of a nucleic acid sample is used. Therefore, in the nucleic acid detection method using a nucleic acid microarray, by using the composition as the nucleic acid sample, it is possible to reduce the adverse influence of the first to sixth peptide fragments, thus enabling remarkable improvement in the detection sensitivity of the target nucleic acid.

Production Method

The composition can be produced by separating the first to sixth peptide fragments from an alkaline phosphatase extract from an organ of a bovine, a shrimp and the like, an alkaline phosphatase extract from a microorganism into which a gene encoding an alkaline phosphatase has been introduced, a bacterial cell homogenate of a microorganism into which a gene encoding an alkaline phosphatase has been introduced, a commercially available alkaline phosphatase product and the like. Examples of the method of separating the first to sixth peptide fragments include dialysis, salting out, gel filtration, ultrafiltration, membrane separation, ion exchange, column chromatography, electrophoresis and the like. Regarding the method of separating the first to sixth peptide fragments, one separation method may be used alone, or two or more separation methods may be used in combination. For example, by purifying a commercially available alkaline phosphatase product by column chromatography or the like, it is possible to make the content of the first to sixth peptide fragments to the alkaline phosphatase be to a desired range. The column chromatography is, for example, liquid chromatography. The column and the mobile phase used in liquid chromatography is not particularly limited as long as the first to sixth peptide fragments can be separated, and it is preferable to use a C18-supported reverse-phase column. The seventh to ninth peptide fragments can also be separated in the same manner as for the first to sixth peptide fragments.

Use

The composition can be used for various methods requiring an alkaline phosphatase activity.

In one example, the composition is used for a method of producing a dephosphorylated nucleic acid, the method including the steps of:
providing the composition;
providing a nucleic acid; and
treating the nucleic acid with the composition to dephosphorylate the nucleic acid. The first to sixth peptide fragments coexisting in the alkaline phosphatase have a possibility of adversely influencing when the nucleic acid is dephosphorylated by the alkaline phosphatase. In this regard, in the composition, the content ratios of the first to sixth peptide fragments to the alkaline phosphatase satisfy formulas (1) to (6), respectively. In other words, in the composition, the relative contents of the first to sixth peptide fragments have been reduced. Thus, by treating the nucleic acid with the composition, it is possible to improve the dephosphorylation efficiency of the nucleic acid.

In one example, the composition is used for a method of producing a labeled nucleic acid, the method including the steps of:
providing the composition;
providing a nucleic acid;
providing a labeling substance;
treating the nucleic acid with the composition to dephosphorylate the nucleic acid; and
binding the labeling substance to the dephosphorylated nucleic acid. The first to sixth peptide fragments coexisting in the alkaline phosphatase have a possibility of adversely influencing when the nucleic acid is dephosphorylated by the alkaline phosphatase and/or when the labeling substance is bound to the dephosphorylated nucleic acid. In this regard, in the composition, the content ratios of the first to sixth peptide fragments to the alkaline phosphatase satisfy formulas (1) to (6), respectively. In other words, in the composition, the relative contents of the first to sixth peptide fragments have been reduced. Thus, by treating the nucleic acid with the composition, it is possible to improve the dephosphorylation efficiency of the nucleic acid and/or the labeling efficiency of the dephosphorylated nucleic acid.

In the step of treating the nucleic acid with the composition to dephosphorylate the nucleic acid, the reaction conditions can be appropriately adjusted. The reaction time is usually 10 to 60 minutes, and preferably 20 to 50 minutes. The reaction temperature is usually 20 to 60° C., and preferably 25 to 45° C. The reaction is usually performed in an aqueous vehicle such as water. The nucleic acid is, for example, DNA, RNA and the like. When the nucleic acid is treated with the composition, the 5' end and/or the 3' end of the nucleic acid is dephosphorylated.

In the step of binding the labeling substance to the dephosphorylated nucleic acid, as the labeling substance, for example, a fluorescent dye, a fluorescent protein, a chemiluminescent body, a metal complex, a metal fine particle, biotin, a radioisotope and the like, can be used. The reaction conditions can be appropriately adjusted according to the type of the labeling substance. The dephosphorylated nucleic acid has a 5' end and/or a 3' end, each of which has been dephosphorylated by the alkaline phosphatase, and the labeling substance can be bound to the dephosphorylated 5' end and/or 3' end.

EXAMPLES

Our compositions and methods will be described in detail by way of Examples, but this disclosure is not limited to the following Examples.

Conditions of LC-MS/MS Analysis
Conditions of the LC-MS/MS analysis used in Examples and Comparative Examples were as follows.
Apparatus Configuration
Mass spectrometer: maXis impact (manufactured by Bruker Daltnics, Inc.)
Conditions of Mass Spectrometry
Ionization method: ESI
Measured ion: cation
Capillary voltage: 4,500 V
Nebulizer: 2.0 bar
Dry gas: 8.0 L/min
Detector voltage: 1,823 V
Measuring span (MS): m/z 50 to 2,200
MS/MS Conditions
Measuring span (MS): m/z 50 to 2,200
Collision gas: nitrogen
Conditions of LC-UV Analysis
Conditions of the LC-UV analysis used in Examples and Comparative Examples were as follows.
Apparatus Configuration
Liquid chromatograph: LC-30A system (manufactured by Shimadzu Corporation)
Detector: UV-Vis (190 to 900 nm, manufactured by Shimadzu Corporation)
Conditions of Liquid Chromatography
Column: Acquity BEH C18 1.7 μm (manufactured by Waters Corporation)
Column size: 2.1 mm×100 mm
Column temperature: 50° C.
Mobile phase flow rate: 0.2 mL/min
Mobile phase A: mixed solution of water/formic acid (1000:1)
Mobile phase B: mixed solution of acetonitrile/water/formic acid (900:100:1)
Injection volume: 20 μL
Gradient Program:

TABLE 2

| Times (min) | Mobile phase A (vol %) | Mobile phase B (vol %) |
|---|---|---|
| 0 | 100 | 0 |
| 10 | 100 | 0 |
| 40 | 35 | 65 |
| 40.1 | 0 | 100 |
| 50 | 0 | 100 |
| 50.1 | 100 | 0 |
| 60 | 100 | 0 |

Nucleic Acid Detection Method
The nucleic acid detection method used in Examples and Comparative Examples was as follows.
The detection method of a nucleic acid was performed by using a DNA chip (DNA microarray). Specifically, detection was performed by using "3D-Gene" human miRNA oligo chip (compatible with miRBase release 21) manufactured by Toray Industries, Inc.

Comparative Examples 1 to 8

Eight alkaline phosphatase products purchased from five companies (referred to as "composition C1" to "composition C8") were used as the alkaline phosphatase compositions of Comparative Examples 1 to 8. The alkaline phosphatase contained in each of the compositions C1 to C8 was an alkaline phosphatase derived from the intestinal tract of a bovine. When the alkaline phosphatase specific activities of the compositions C1 to C8 were measured, they were 2,238 U/mg for the composition C1, 2,492 U/mg for the composition C2, 2,431 U/mg for the composition C3, 2,519 U/mg for the composition C4, 2,411 U/mg for the composition C5, 2,552 U/mg for the composition C6, 2,448 U/mg for the composition C7, and 2,490 U/mg for the composition C8. The alkaline phosphatase specific activities were measured by a method using p-nitrophenylphosphate. Specifically, the method was as follows.

The following solutions A and B were provided:
Solution A: 1M diethanolamine buffer (pH 9.8)
Solution B: aqueous 0.67M p-nitrophenolphosphate solution.
2.9 mL of the solution A and 0.1 mL of the solution B were prepared in a cuvette (optical path length=1 cm), and warmed at 37° C. for 5 minutes. Then, 0.1 mL of an aqueous alkaline phosphatase solution was added, and the absorbance change at 405 nm (37° C.) was measured with a spectrophotometer for 3 to 5 minutes to obtain an absorbance change per unit time ($\Delta OD$). By using as a control, a sample to which water was added in place of the aqueous alkaline phosphatase solution, the absorbance change was obtained ($\Delta OD$ blank). The alkaline phosphatase activity (U/mL) was calculated from the formula:

Alkaline phosphatase activity (U/mL)=($\Delta OD - \Delta OD$ blank)×3.1/(18.2×0.1×1.0).

The concentration of the alkaline phosphatase in the aqueous alkaline phosphatase solution was calculated by measuring the absorbance at 214 nm. The aqueous alkaline phosphatase solution was diluted with distilled water so that the absorbance at 214 nm became 0.1 to 1.0, and 1 Abs was approximated to 1 mg/mL, and then the value obtained by multiplying by the dilution rate was regarded as the concentration of the alkaline phosphatase. The specific activity represents an activity (U/mg) per 1 mg of the alkaline phosphatase, and was calculated by the abovementioned measurement method.

An aqueous 10% by weight alkaline phosphatase solution was prepared from each of the compositions C1 to C8, and by using this aqueous solution, an LC-UV analysis and an LC-MS/MS analysis were performed. Based on the extracted ion chromatogram obtained by the LC-MS/MS analysis, the peak area value of each of the first peptide fragment consisting of the amino acid sequence set forth in SEQ ID NO: 1, the second peptide fragment consisting of the amino acid sequence set forth in SEQ ID NO: 2, the third peptide fragment consisting of the amino acid sequence set forth in SEQ ID NO: 3, the fourth peptide fragment consisting of the amino acid sequence set forth in SEQ ID NO: 4, the fifth peptide fragment consisting of the amino acid sequence set forth in SEQ ID NO: 5, the sixth peptide fragment consisting of the amino acid sequence set forth in SEQ ID NO: 6, the seventh peptide fragment consisting of the amino acid sequence set forth in SEQ ID NO: 7, the eighth peptide fragment consisting of the amino acid sequence set forth in SEQ ID NO: 8 and the ninth peptide fragment consisting of the amino acid sequence set forth in SEQ ID NO: 9 was calculated by an automatic integration method. Based on the chromatogram obtained by the LC-UV analysis, the peak area value of the alkaline phosphatase was calculated by an automatic integration method. In the LC-UV analysis, the alkaline phosphatase was detected as a component having absorption at 214 nm.

FIG. 1 shows an extracted ion chromatogram on the first peptide fragment obtained by an LC-MS/MS analysis of the composition C2 in Comparative Example 2.

Figure 2:
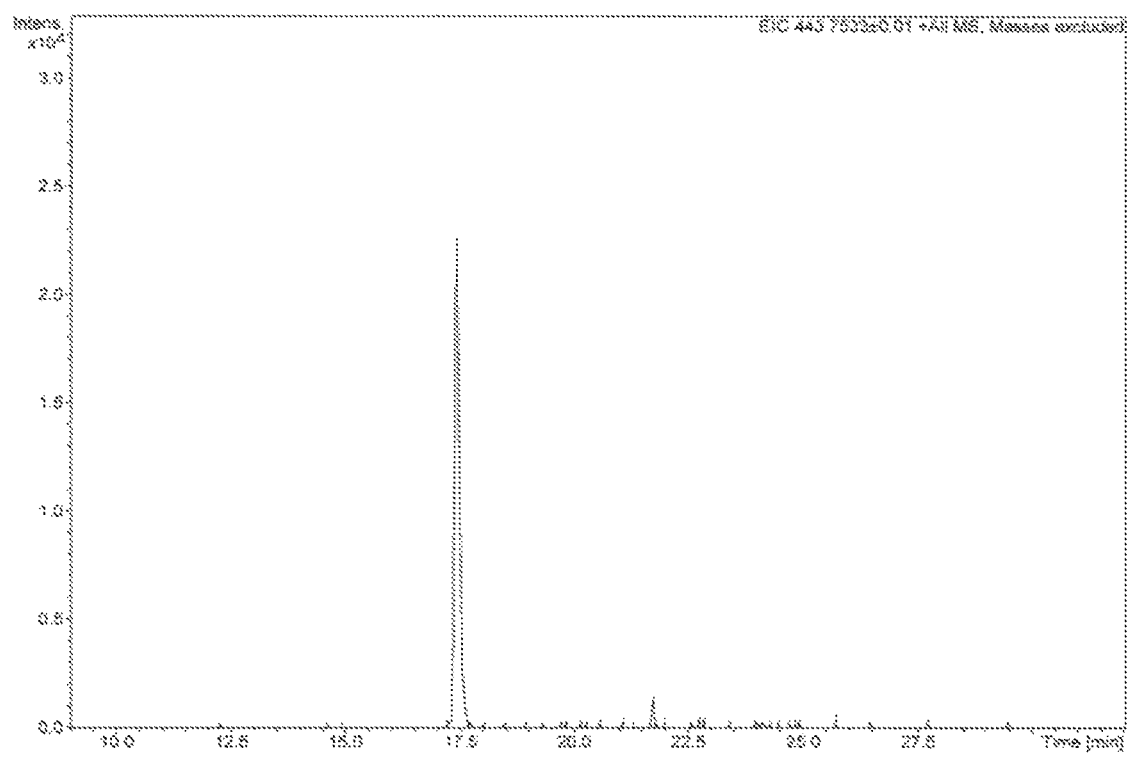
FIG. 2 shows an extracted ion chromatogram on the second peptide fragment obtained by an LC-MS/MS analysis of the composition C2 in Comparative Example 2.

FIG. 2 shows an extracted ion chromatogram on the second peptide fragment obtained by an LC-MS/MS analysis of the composition C2 in Comparative Example 2.

Figure 3:
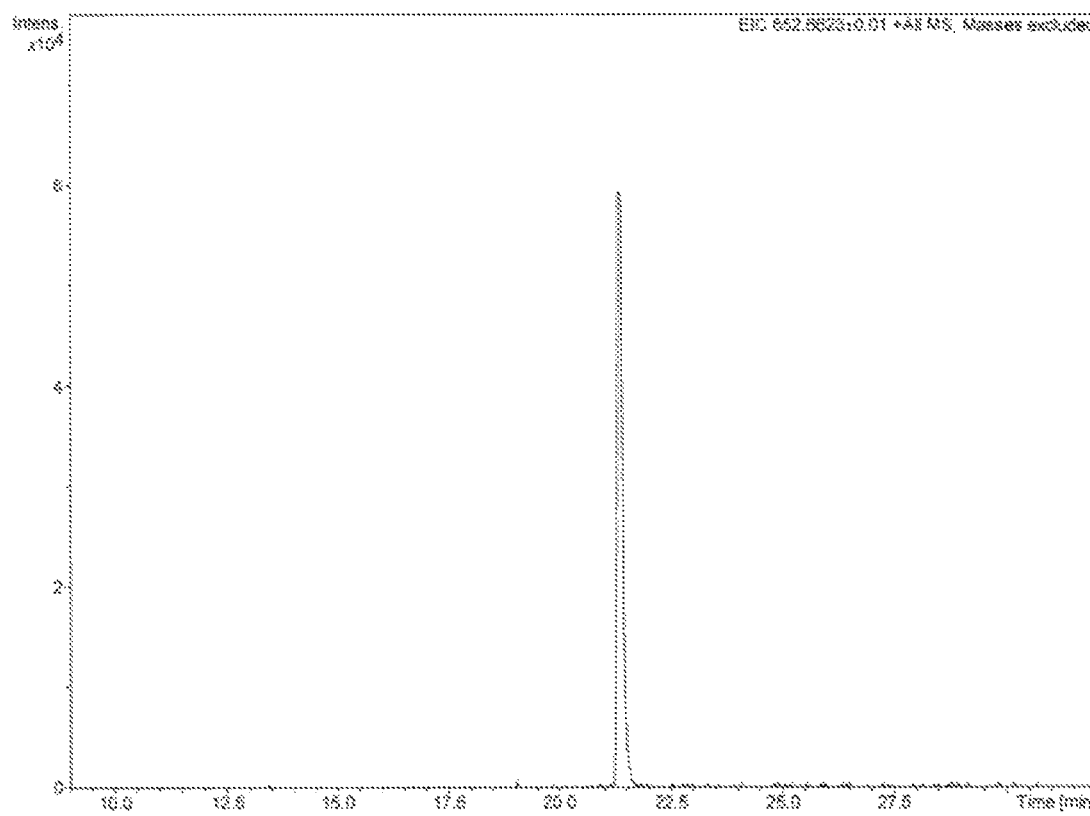
FIG. 3 shows an extracted ion chromatogram on the third peptide fragment obtained by an LC-MS/MS analysis of the composition C2 in Comparative Example 2.

FIG. 3 shows an extracted ion chromatogram on the third peptide fragment obtained by an LC-MS/MS analysis of the composition C2 in Comparative Example 2.

Figure 4:
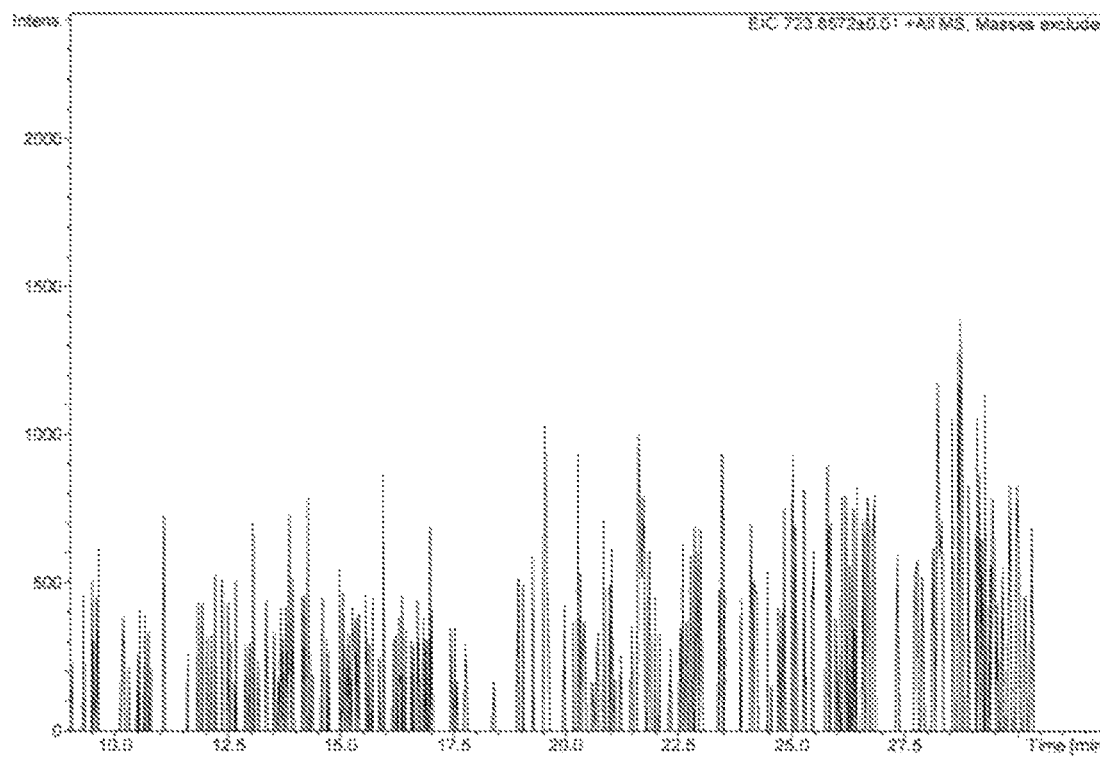
FIG. 4 shows an extracted ion chromatogram on the fourth peptide fragment obtained by an LC-MS/MS analysis of the composition C2 in Comparative Example 2.

FIG. 4 shows an extracted ion chromatogram on the fourth peptide fragment obtained by an LC-MS/MS analysis of the composition C2 in Comparative Example 2.

Figure 5:
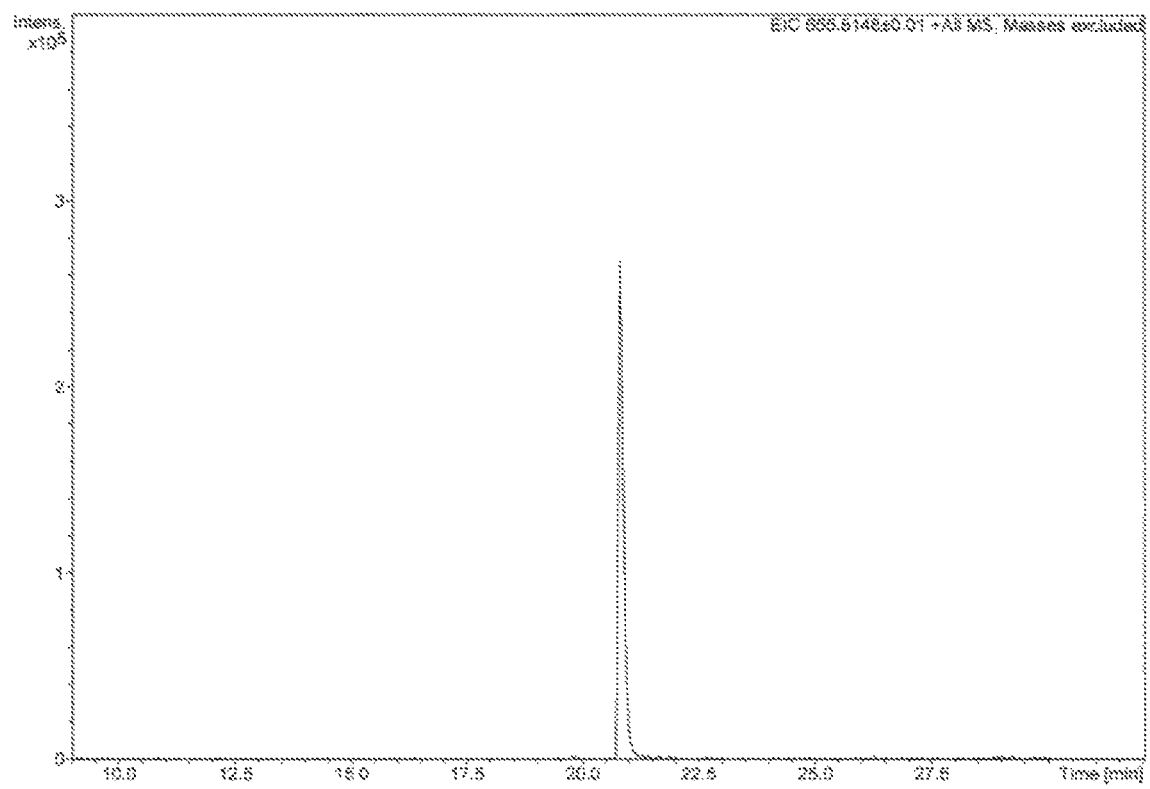
FIG. 5 shows an extracted ion chromatogram on the fifth peptide fragment obtained by an LC-MS/MS analysis of the composition C2 in Comparative Example 2.

FIG. 5 shows an extracted ion chromatogram on the fifth peptide fragment obtained by an LC-MS/MS analysis of the composition C2 in Comparative Example 2.

Figure 6:
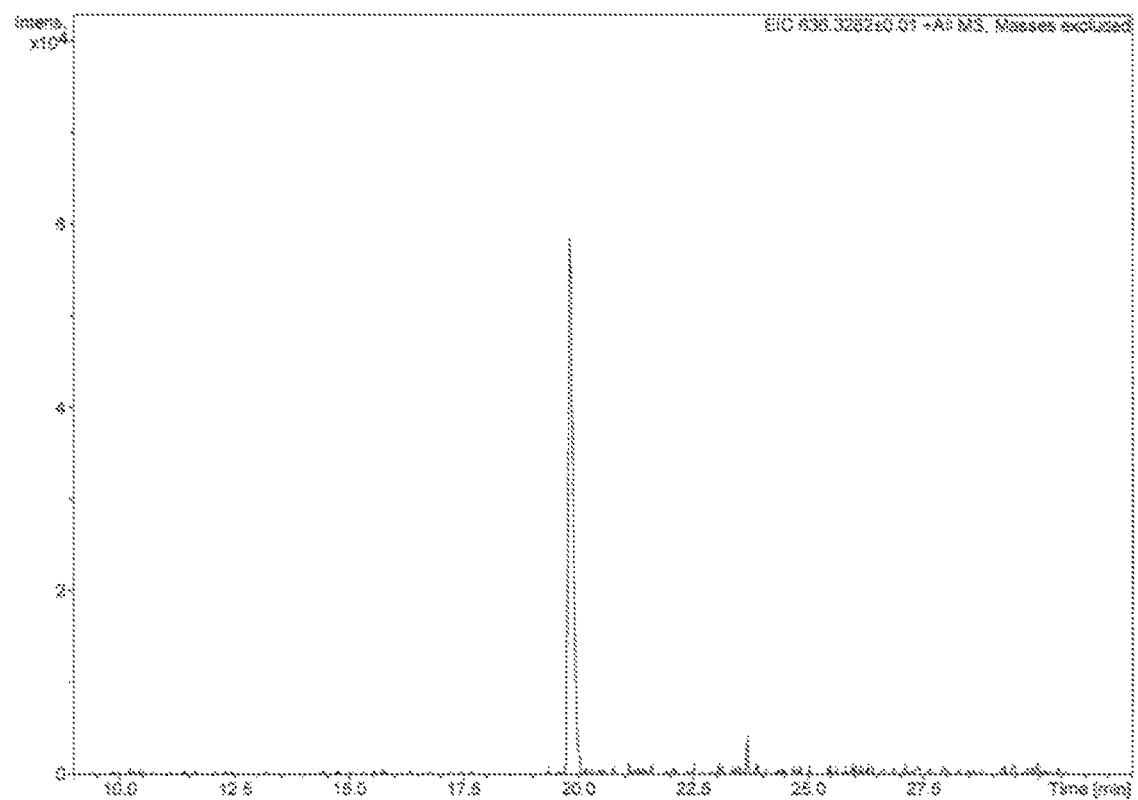
FIG. 6 shows an extracted ion chromatogram on the sixth peptide fragment obtained by an LC-MS/MS analysis of the composition C2 in Comparative Example 2.

FIG. 6 shows an extracted ion chromatogram on the sixth peptide fragment obtained by an LC-MS/MS analysis of the composition C2 in Comparative Example 2.

Figure 7:
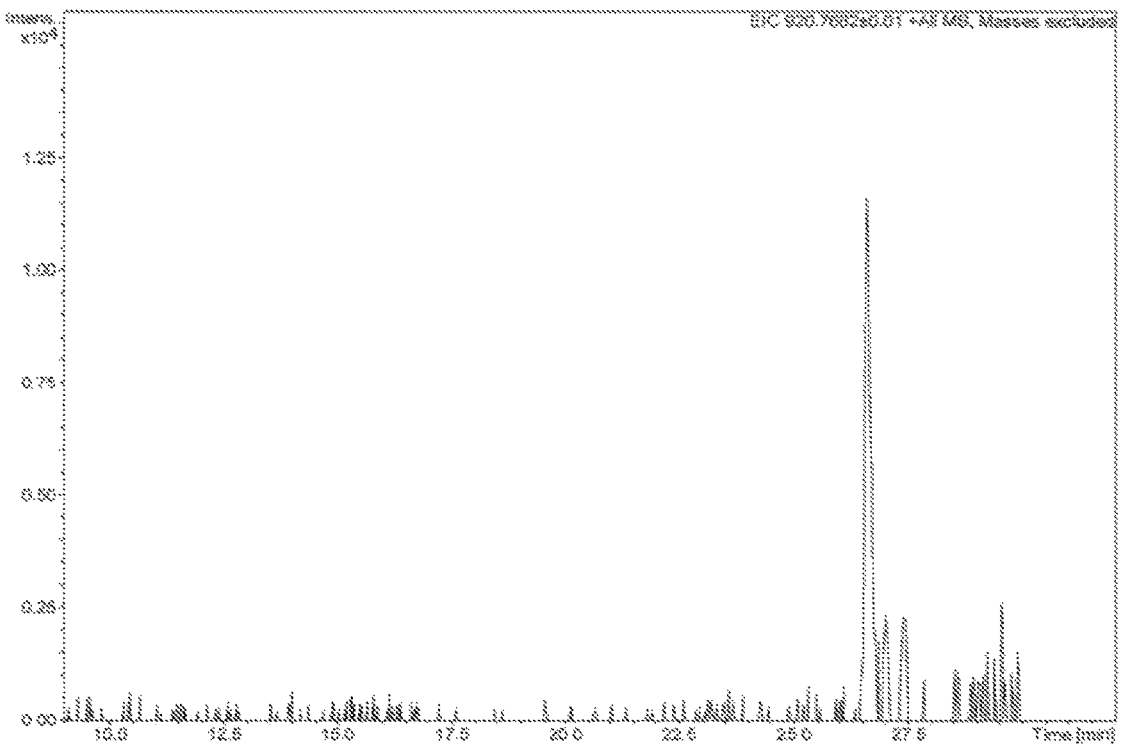
FIG. 7 shows an extracted ion chromatogram on the seventh peptide fragment obtained by an LC-MS/MS analysis of the composition C2 in Comparative Example 2.

FIG. 7 shows an extracted ion chromatogram on the seventh peptide fragment obtained by an LC-MS/MS analysis of the composition C2 in Comparative Example 2.

Figure 8:
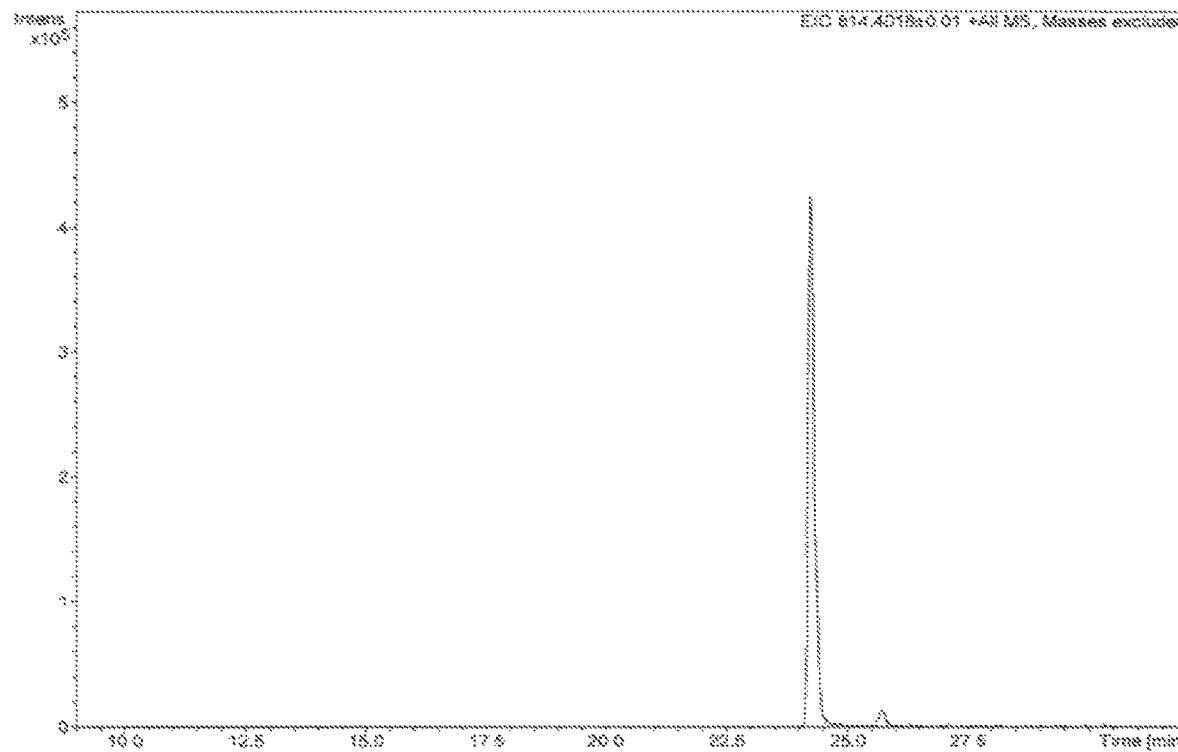
FIG. 8 shows an extracted ion chromatogram on the eighth peptide fragment obtained by an LC-MS/MS analysis of the composition C2 in Comparative Example 2.

FIG. 8 shows an extracted ion chromatogram on the eighth peptide fragment obtained by an LC-MS/MS analysis of the composition C2 in Comparative Example 2.

Figure 9:
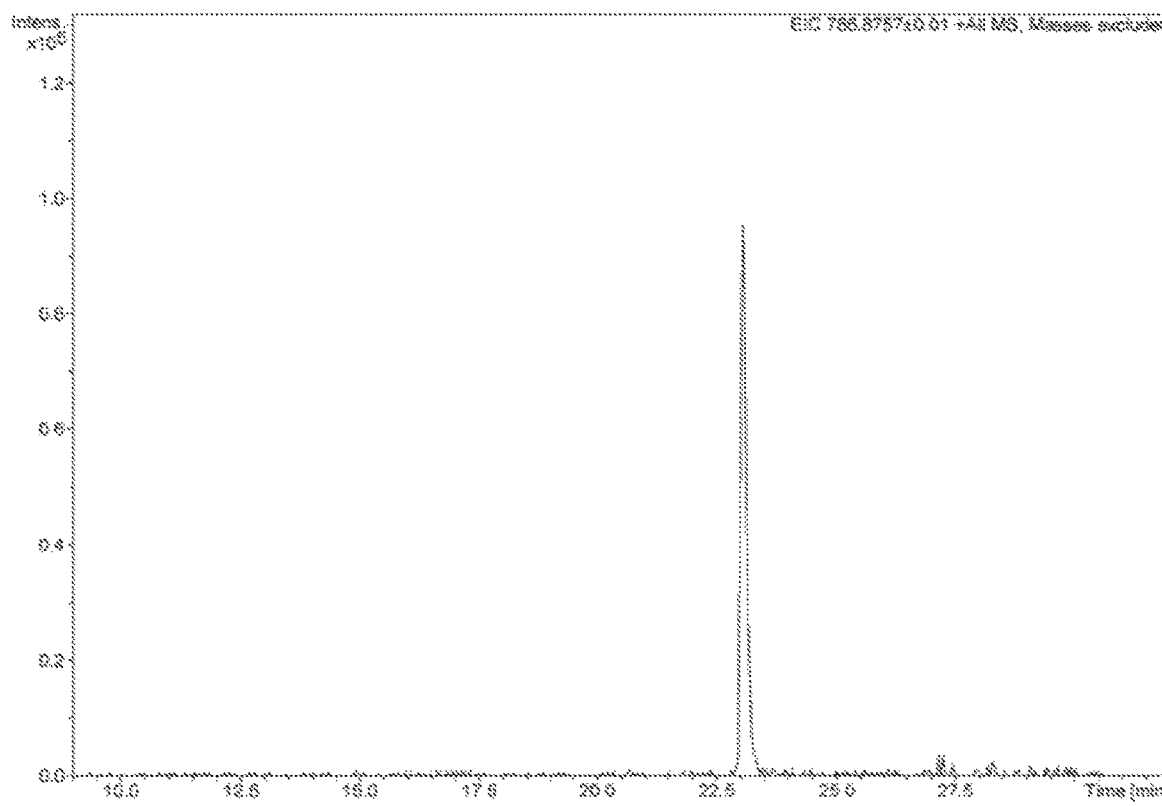
FIG. 9 shows an extracted ion chromatogram on the ninth peptide fragment obtained by an LC-MS/MS analysis of the composition C2 in Comparative Example 2.

FIG. 9 shows an extracted ion chromatogram on the ninth peptide fragment obtained by an LC-MS/MS analysis of the composition C2 in Comparative Example 2.

By using each of the alkaline phosphatase compositions of Comparative Examples 1 to 8, a nucleic acid was dephosphorylated, and the obtained dephosphorylated nucleic acid was labeled with a cyanine-based organic fluorescent dye. Specifically, dephosphorylation reaction and labeling reaction were performed as follows.

Whole blood collected from a healthy individual was centrifuged to obtain 1 mL of serum. From the serum, microRNA was extracted by using the "3D-Gene" RNA extraction reagent from liquid sample kit (manufactured by Toray Industries, Inc.). The obtained extracted microRNA was regarded as a mother liquor and was labeled by using "3D-Gene" miRNA labeling kit (manufactured by Toray Industries, Inc.). Specifically, 5 µL of the obtained extracted microRNA was added to a mixed solution of 0.4 µL of AP buffer and 1.0 µL of Spike Control of the abovementioned kit, and 0.4 µL of the composition C1 was further added to prepare a solution. Then, the prepared solution was incubated at 37° C. for 40 minutes, followed by allowing to stand on ice for 2 minutes. Then, 1.2 µL of LE Buffer, 3.0 µL of 3D-Gene Fluorescent Label, 2.5 µL of Nuclease free water and 1.0 µL of Labeling enzyme were added, and the obtained solution was incubated at 16° C. for 1 hour, followed by incubation at 65° C. for 15 minutes to obtain a labeled nucleic acid. Dephosphorylation reaction and labeling reaction were performed by using the same method as mentioned above, in which the compositions C2 to C8 and the same extracted microRNA mother liquor were used.

By using the obtained labeled nucleic acid, detection of a nucleic acid was performed. Specifically, for the labeled sample RNA, hybridization was performed by using a DNA chip ("3D-Gene" miRNA chip, manufactured by Toray Industries, Inc.) in accordance with the standard protocol thereof. The DNA chip after hybridization was subjected to a microarray scanner (manufactured by Toray Industries, Inc.) to measure the fluorescence intensity. Regarding the setting of the scanner, the laser output was set at 100%, and the voltage setting of the photomultiplier was set at AUTO setting. Detection of a nucleic acid was performed by using a DNA chip (DNA microarray) as mentioned above. The number of valid spots in the DNA chip was determined to calculate the detection rate (%). Specifically, of a total of 2,588 spots on the DNA chip, spots with a value obtained by subtracting the noise (signal value at a site having no spot) from the detection signal value being 100 or more were regarded as valid spots, and the value obtained by dividing the number of valid spots by the number of all spots and by multiplying by 100 was regarded as the detection rate. The results are shown in Tables 4-2 and 5-2.

Examples 1 to 4

The alkaline phosphatase compositions of Comparative Examples 2 to 4 and 8 (compositions C2 to C4 and C8) were purified by the following method to obtain alkaline phosphatase compositions of Examples 1 to 4 (referred to as "composition E1" to "composition E4"). The purification method was as follows.

Dialysis Step

The composition C2 (30 μL) was dialyzed three times with a dialysis buffer (1 mL, 50 mM Tris-HCl, 2 mM $MgCl_2$, 0.2 mM $ZnCl_2$) by using a dialysis cup (cutoff molecular weight of 3.5 K), and the concentrate was collected.

Gel Filtration Step

The concentrate after dialysis treatment was collected by filtration with a buffer (2.5 mL, 10 mM Tris-HCl, 1 mM $MgCl_2$, 0.1 mM $ZnCl_2$, 50 mM KCl, 55% by weight glycerin) by using a gel filtration column.

Hydrophobic Column Step

From the collected solution after gel filtration, the alkaline phosphatase fraction was collected by using a hydrophobic column under the following conditions.

Mobile phase flow rate: 1.0 mL/min
Mobile phase A: 20 mM disodium hydrogenphosphate, 3M ammonium sulfate (50/50)
Mobile phase B: 20 mM disodium hydrogenphosphate
Detector: UV 214 nm
Gradient Program:

TABLE 3

| Times (min) | Mobile phase A (vol %) | Mobile phase B (vol %) |
|---|---|---|
| 0 | 100 | 0 |
| 3 | 100 | 0 |
| 40 | 0 | 100 |
| 50 | 0 | 100 |
| 55 | 100 | 0 |
| 65 | 100 | 0 |

Dialysis Step

The collected alkaline phosphatase fraction was dialyzed three times under the same conditions as for the abovementioned dialysis, and the concentrate was collected.

Ultrafiltration Step

The collected concentrate was collected by filtration with a buffer (2.5 mL, 10 mM Tris-HCl, 1 mM $MgCl_2$, 0.1 mM $ZnCl_2$, 50 mM KCl, 55% by weight glycerin) by using an ultrafiltration column (cutoff molecular weight of 10 K) to obtain the composition E1.

The compositions E2, E3 and E4 were also obtained from the compositions C3, C4 and C8, respectively, by using the same method as mentioned above.

When the alkaline phosphatase specific activities of the alkaline phosphatase compositions of Examples 1 to 4 were measured, they were 2,490 U/mg for the composition E1, 2,420 U/mg for the composition E2, 2,522 U/mg for the composition E3, and 2,470 U/mg for the composition E4. The alkaline phosphatase specific activities were measured in the same manner as mentioned above.

An aqueous 10% by weight alkaline phosphatase solution was prepared from each of the compositions E1 to E4, and by using this aqueous solution, an LC-UV analysis and an LC-MS/MS analysis were performed. Based on the extracted ion chromatogram obtained by the LC-MS/MS analysis, the peak area value of each of the first peptide fragment consisting of the amino acid sequence set forth in SEQ ID NO: 1, the second peptide fragment consisting of the amino acid sequence set forth in SEQ ID NO: 2, the third peptide fragment consisting of the amino acid sequence set forth in SEQ ID NO: 3, the fourth peptide fragment consisting of the amino acid sequence set forth in SEQ ID NO: 4, the fifth peptide fragment consisting of the amino acid sequence set forth in SEQ ID NO: 5, the sixth peptide fragment consisting of the amino acid sequence set forth in SEQ ID NO: 6, the seventh peptide fragment consisting of the amino acid sequence set forth in SEQ ID NO: 7, the eighth peptide fragment consisting of the amino acid sequence set forth in SEQ ID NO: 8 and the ninth peptide fragment consisting of the amino acid sequence set forth in SEQ ID NO: 9 was calculated by an automatic integration method. Based on the chromatogram obtained by the LC-UV analysis, the peak area value of the alkaline phosphatase was calculated by an automatic integration method. In the LC-UV analysis, the alkaline phosphatase was detected as a component having absorption at 214 nm.

Figure 10:
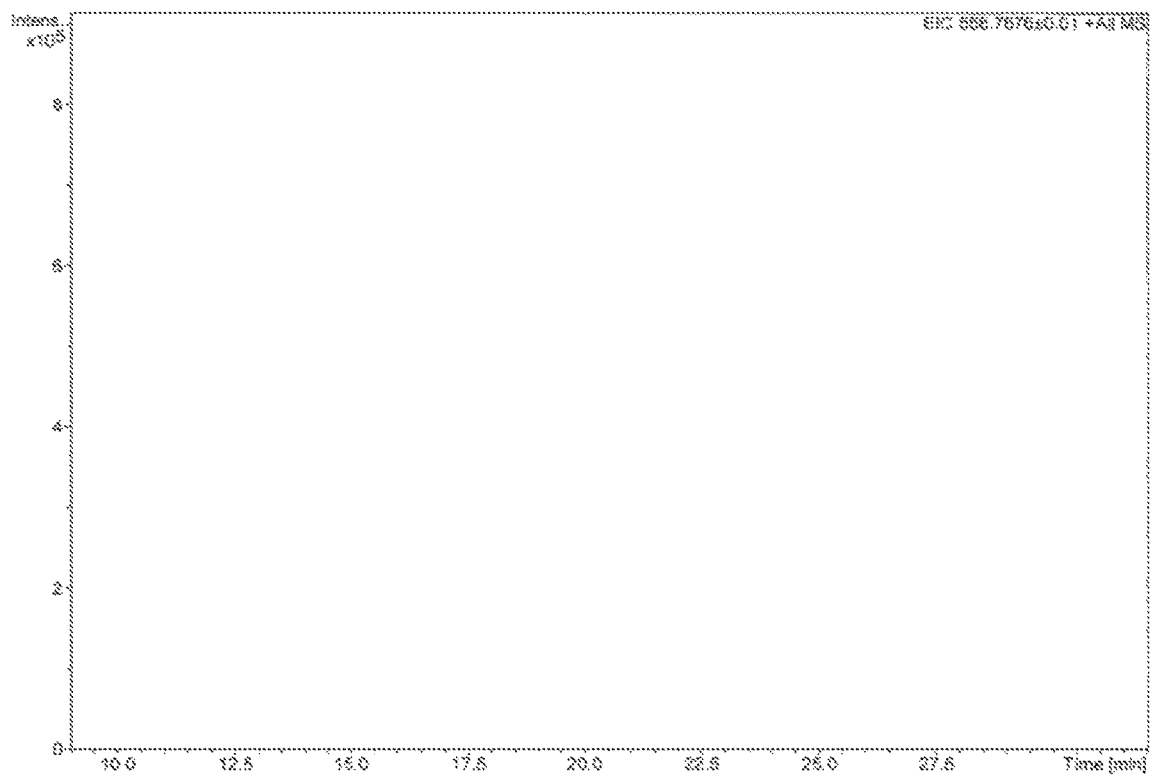
FIG. 10 shows an extracted ion chromatogram on the first peptide fragment obtained by an LC-MS/MS analysis of the composition E1 (purified product of the composition C2) in Example 1.

FIG. 10 shows an extracted ion chromatogram on the first peptide fragment obtained by an LC-MS/MS analysis of the composition E1 (purified product of the composition C2) in Example 1.

Figure 11:
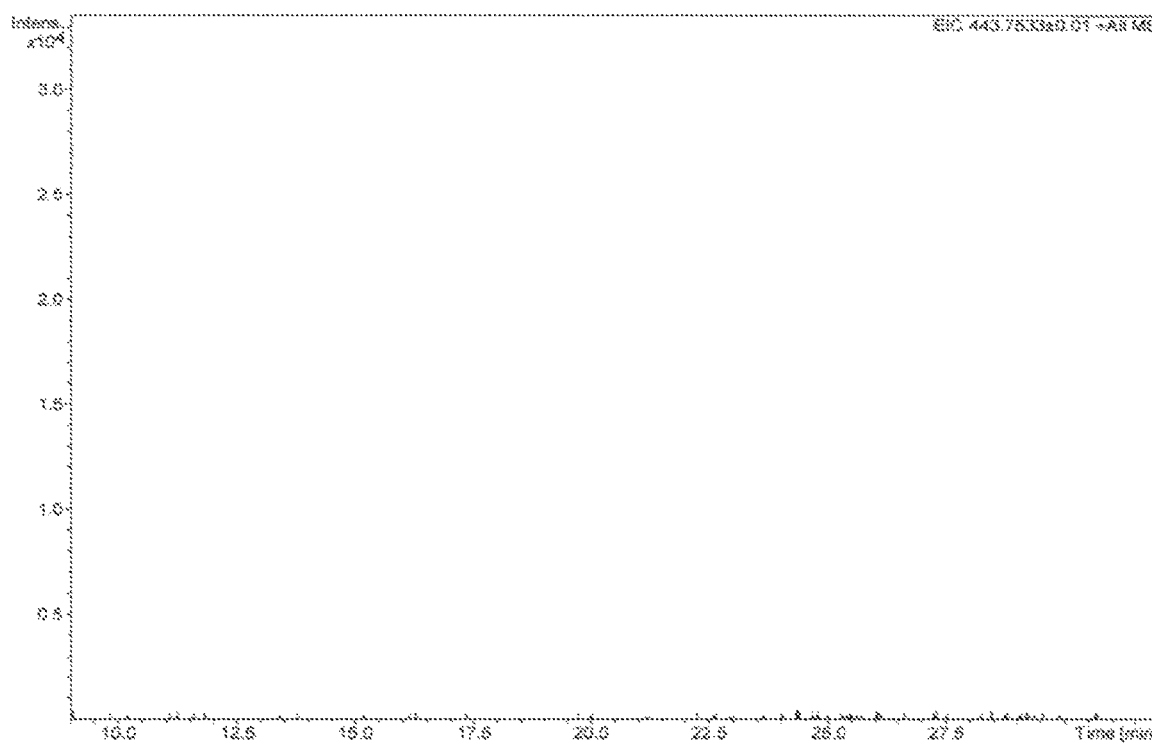
FIG. 11 shows an extracted ion chromatogram on the second peptide fragment obtained by an LC-MS/MS analysis of the composition E1 (purified product of the composition C2) in Example 1.

FIG. 11 shows an extracted ion chromatogram on the second peptide fragment obtained by an LC-MS/MS analysis of the composition E1 (purified product of the composition C2) in Example 1.

Figure 12:
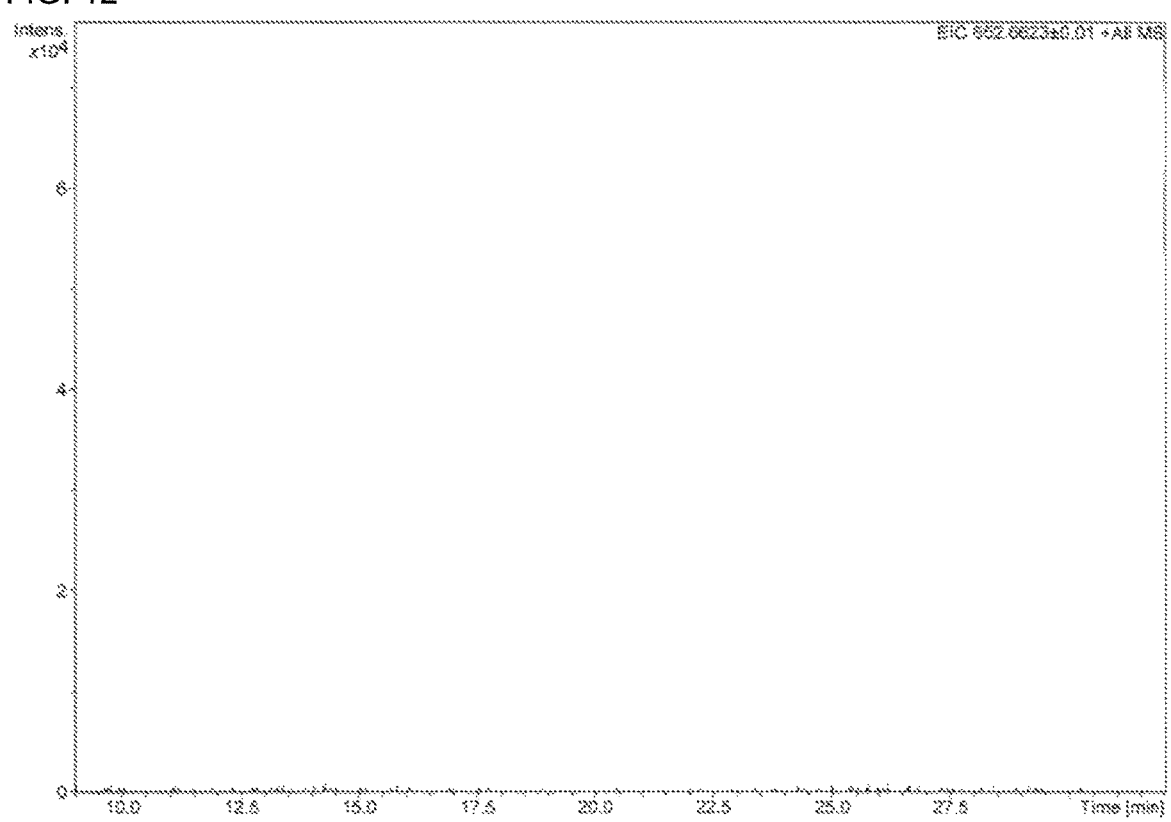
FIG. 12 shows an extracted ion chromatogram on the third peptide fragment obtained by an LC-MS/MS analysis of the composition E1 (purified product of the composition C2) in Example 1.

FIG. 12 shows an extracted ion chromatogram on the third peptide fragment obtained by an LC-MS/MS analysis of the composition E1 (purified product of the composition C2) in Example 1.

Figure 13:
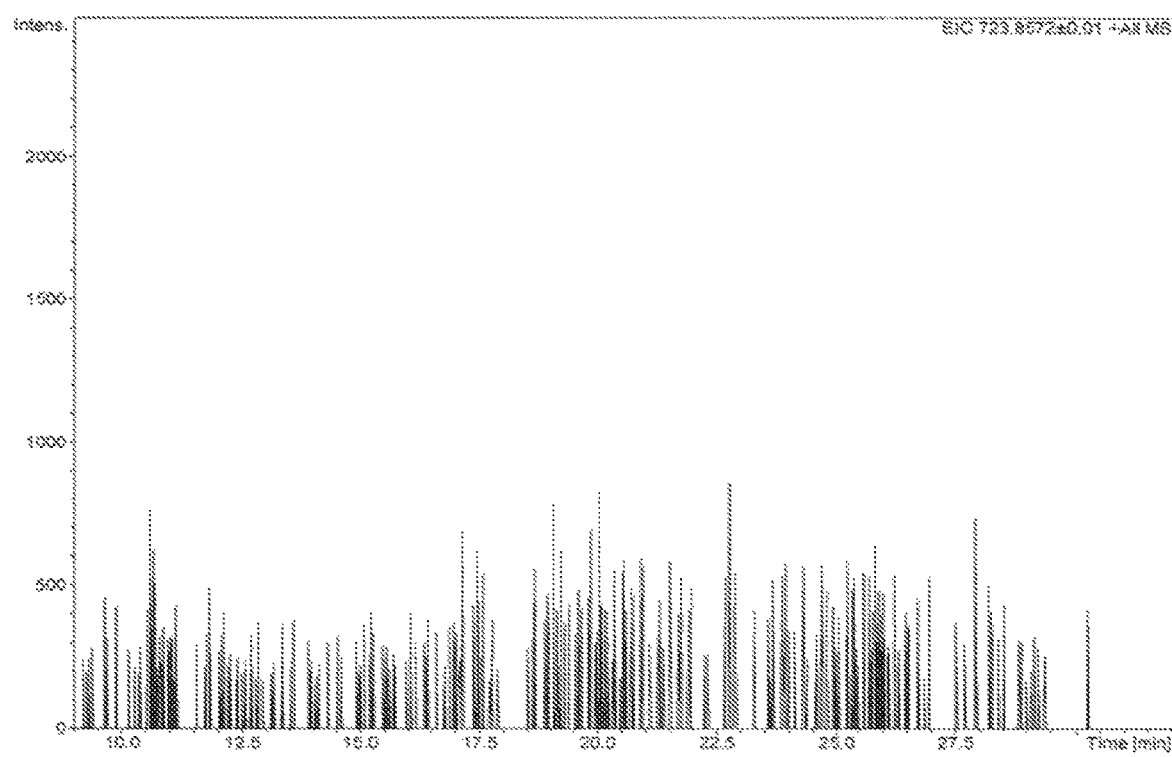
FIG. 13 shows an extracted ion chromatogram on the fourth peptide fragment obtained by an LC-MS/MS analysis of the composition E1 (purified product of the composition C2) in Example 1.

FIG. 13 shows an extracted ion chromatogram on the fourth peptide fragment obtained by an LC-MS/MS analysis of the composition E1 (purified product of the composition C2) in Example 1.

Figure 14:
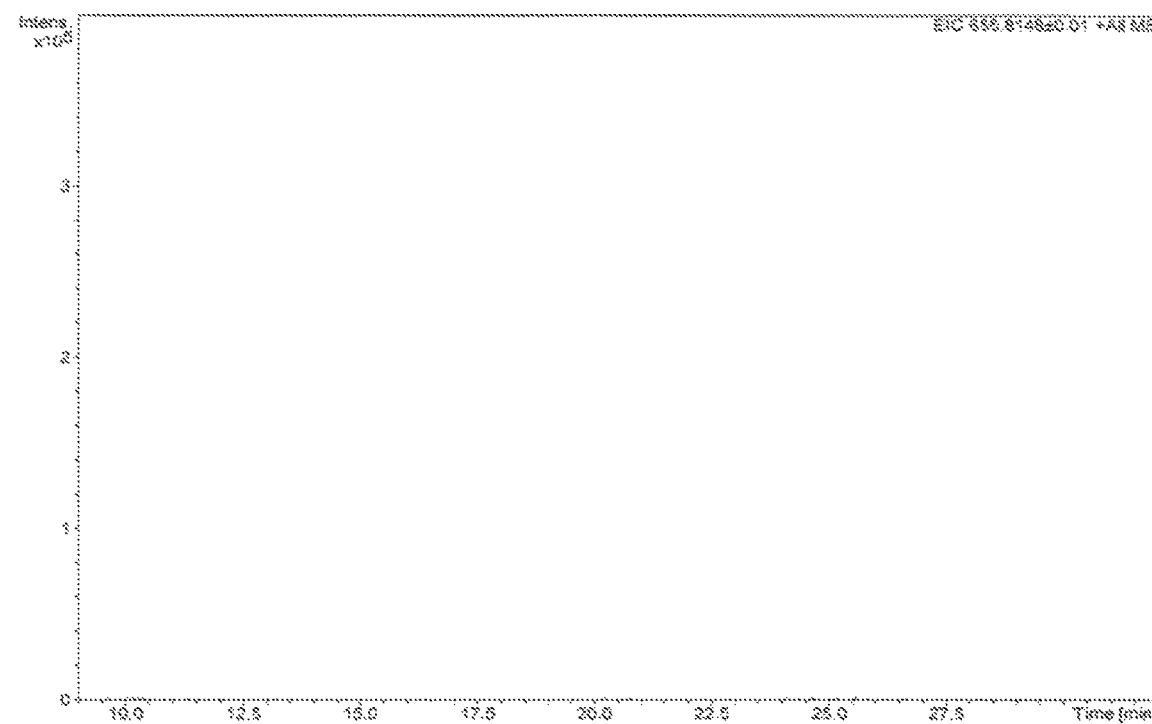
FIG. 14 shows an extracted ion chromatogram on the fifth peptide fragment obtained by an LC-MS/MS analysis of the composition E1 (purified product of the composition C2) in Example 1.

FIG. 14 shows an extracted ion chromatogram on the fifth peptide fragment obtained by an LC-MS/MS analysis of the composition E1 (purified product of the composition C2) in Example 1.

Figure 15:
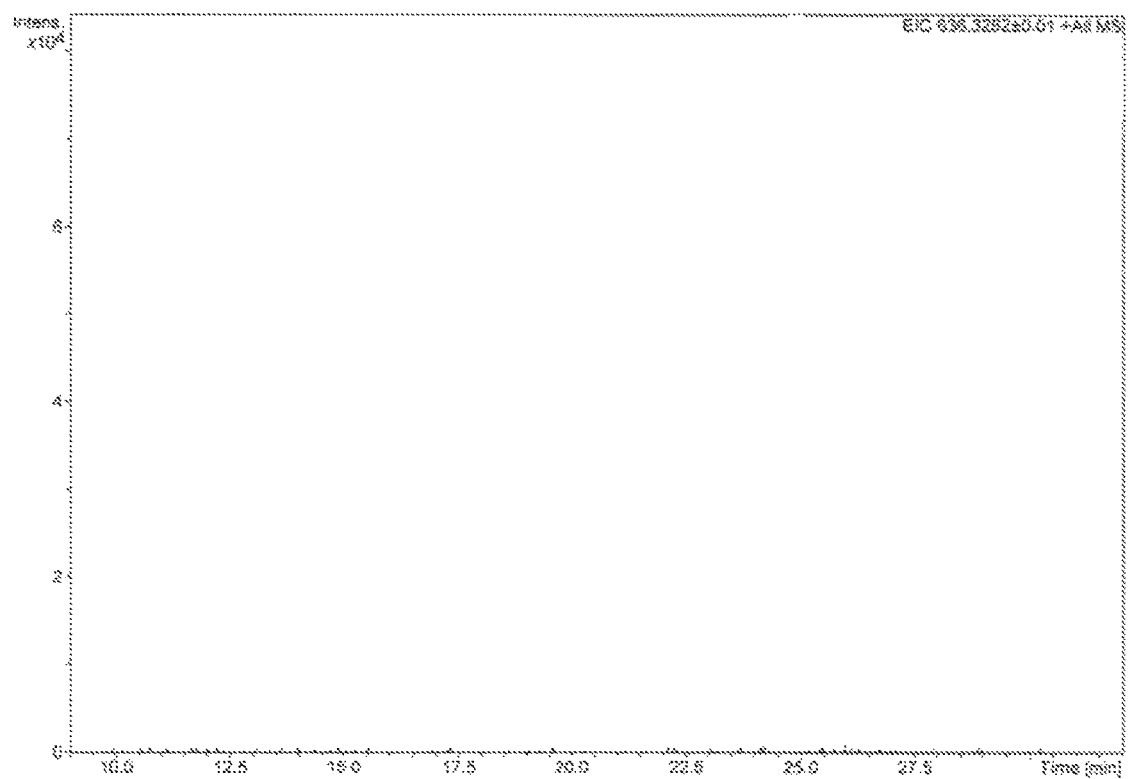
FIG. 15 shows an extracted ion chromatogram on the sixth peptide fragment obtained by an LC-MS/MS analysis of the composition E1 (purified product of the composition C2) in Example 1.

FIG. 15 shows an extracted ion chromatogram on the sixth peptide fragment obtained by an LC-MS/MS analysis of the composition E1 (purified product of the composition C2) in Example 1.

Figure 16:
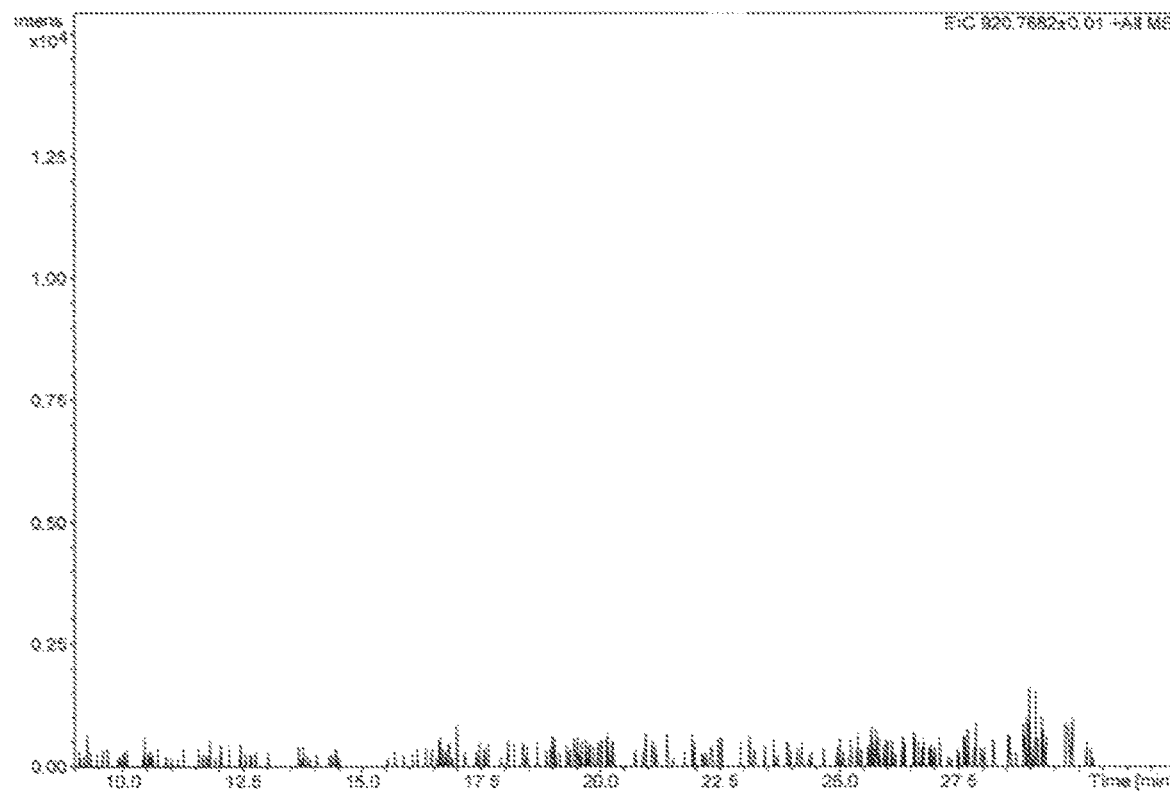
FIG. 16 shows an extracted ion chromatogram on the seventh peptide fragment obtained by an LC-MS/MS analysis of the composition E1 (purified product of the composition C2) in Example 1.

FIG. 16 shows an extracted ion chromatogram on the seventh peptide fragment obtained by an LC-MS/MS analysis of the composition E1 (purified product of the composition C2) in Example 1.

Figure 17:
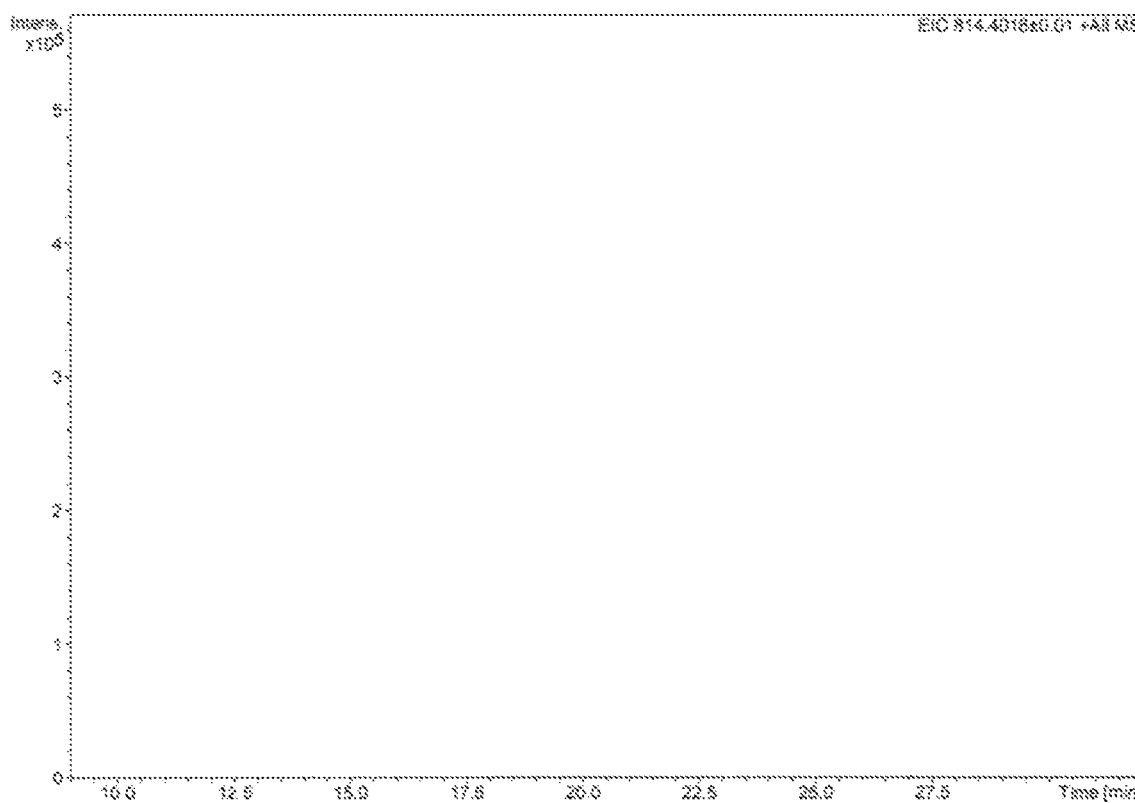
FIG. 17 shows an extracted ion chromatogram on the eighth peptide fragment obtained by an LC-MS/MS analysis of the composition E1 (purified product of the composition C2) in Example 1.

FIG. 17 shows an extracted ion chromatogram on the eighth peptide fragment obtained by an LC-MS/MS analysis of the composition E1 (purified product of the composition C2) in Example 1.

Figure 18:
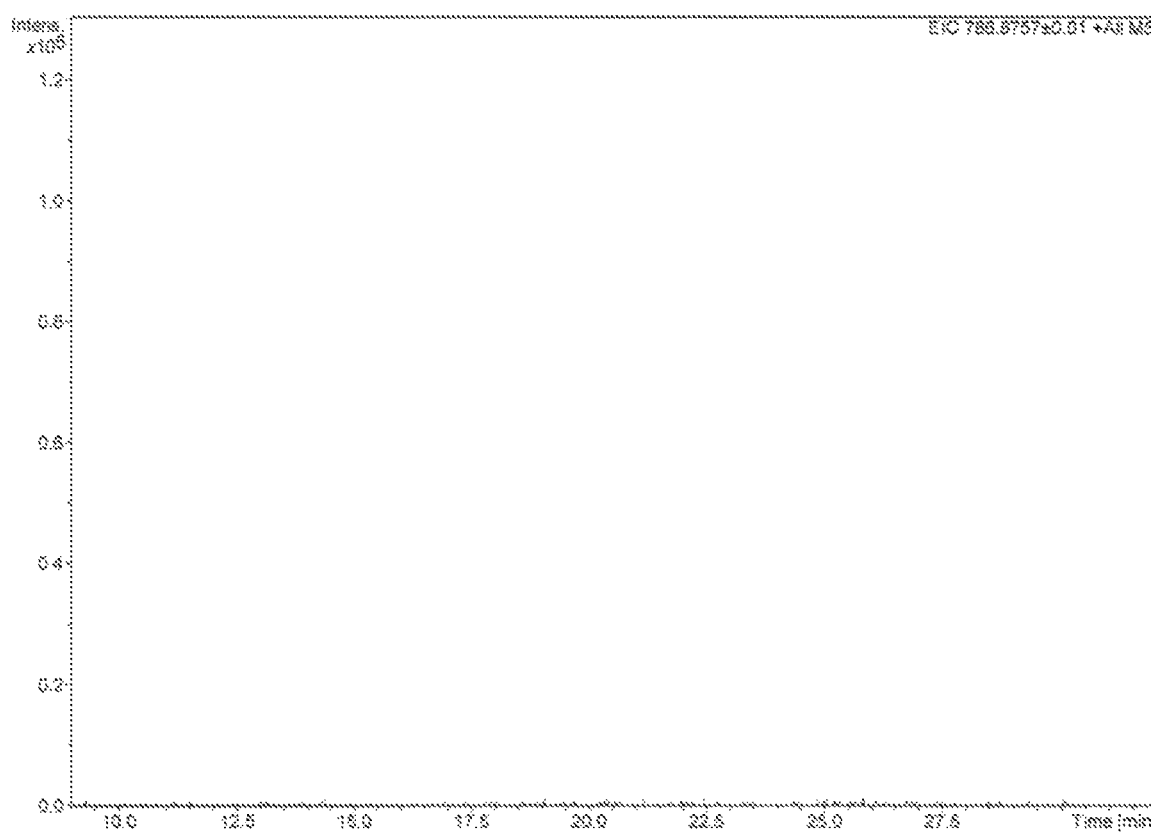
FIG. 18 shows an extracted ion chromatogram on the ninth peptide fragment obtained by an LC-MS/MS analysis of the composition E1 (purified product of the composition C2) in Example 1.

FIG. 18 shows an extracted ion chromatogram on the ninth peptide fragment obtained by an LC-MS/MS analysis of the composition E1 (purified product of the composition C2) in Example 1.

Figure 19:
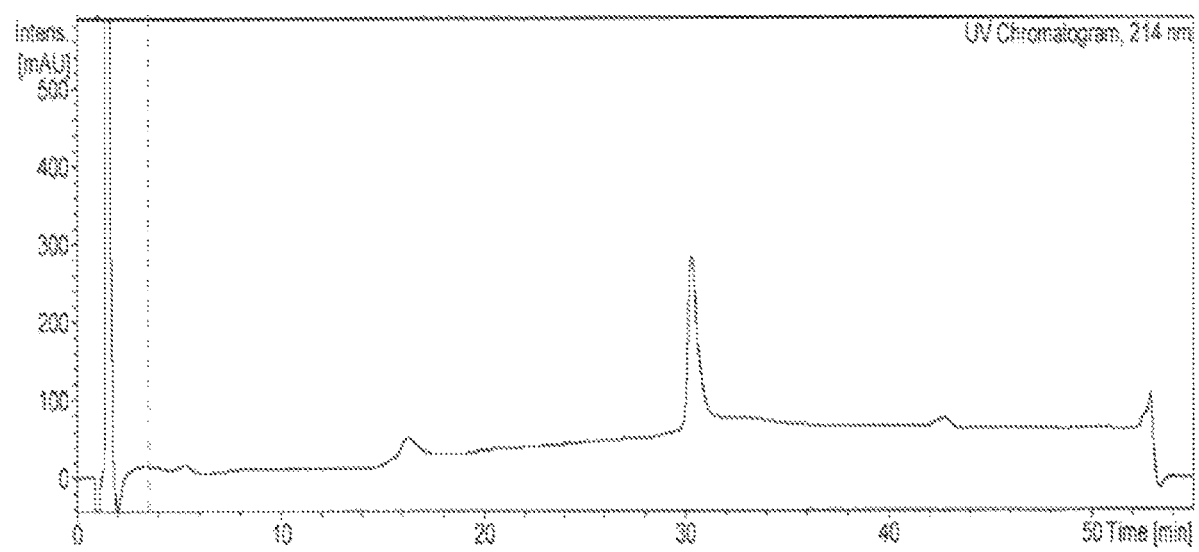
FIG. 19 shows a chromatogram on an alkaline phosphatase obtained by an LC-UV analysis of the composition E1 (purified product of the composition C2) in Example 1.

FIG. 19 shows a chromatogram on an alkaline phosphatase obtained by an LC-UV analysis of the composition E1 (purified product of the composition C2) in Example 1. It is noted that a chromatogram on an alkaline phosphatase obtained by an LC-UV analysis of each of the composition in Examples 2 to 4 and Comparative Examples 1 to 8 was the same as FIG. 19.

By using the alkaline phosphatase compositions of Examples 1 to 4, a nucleic acid was dephosphorylated, and the obtained dephosphorylated nucleic acid was labeled with a cyanine-based organic fluorescent dye. Dephosphorylation reaction and labeling reaction were performed in the same manner as mentioned above.

By using the obtained labeled nucleic acid, detection of a nucleic acid was performed. Detection of a nucleic acid was performed by using a DNA chip (DNA microarray) as mentioned above. The number of valid spots in the DNA chip was determined to calculate the detection rate (%). The results are shown in Tables 4-1 and 5-1.

TABLE 4-1

| | Examples | | | |
|---|---|---|---|---|
| | 1 | 2 | 3 | 4 |
| Peak area value of First peptide fragment ($X_1$) | 230 | 200 | 200 | 200 |
| Peak area value of Second peptide fragment ($X_2$) | 200 | 200 | 200 | 200 |
| Peak area value of Third peptide fragment ($X_3$) | 226 | 226 | 360 | 200 |
| Peak area value of Fourth peptide fragment ($X_4$) | 1272 | 884 | 1616 | 280 |
| Peak area value of Fifth peptide fragment ($X_5$) | 1766 | 949 | 1769 | 585 |
| Peak area value of Sixth peptide fragment ($X_6$) | 668 | 367 | 736 | 278 |
| Peak area value of Seventh peptide fragment ($X_7$) | 1056 | 2637 | 513 | 798 |
| Peak area value of Eighth peptide fragment ($X_8$) | 1783 | 517 | 2416 | 246 |
| Peak area value of Ninth peptide fragment ($X_9$) | 376 | 940 | 5964 | 793 |
| Peak area value of Alkaline phosphatase (Y) | 263754 | 268264 | 267135 | 258635 |

TABLE 4-2

| | Comparative Examples | | | | | | | |
|---|---|---|---|---|---|---|---|---|
| | 1 | 2 | 3 | 4 | 5 | 6 | 7 | 8 |
| Peak area value of First peptide fragment ($X_1$) | 10940 | 1594116 | 145105 | 16140 | 1543 | 1765 | 13135 | 311710 |
| Peak area value of Second peptide fragment ($X_2$) | 670 | 5794 | 2942 | 377 | 1367 | 472 | 4549 | 4550 |
| Peak area value of Third peptide fragment ($X_3$) | 5580 | 637579 | 37977 | 78293 | 2662 | 481 | 12520 | 107131 |
| Peak area value of Fourth peptide fragment ($X_4$) | 2279 | 3389 | 3647 | 1887 | 10718 | 2944 | 9570 | 6445 |
| Peak area value of Fifth peptide fragment ($X_5$) | 4536 | 281119 | 5945 | 124326 | 17235 | 6523 | 118914 | 672270 |
| Peak area value of Sixth peptide fragment ($X_6$) | 1050 | 564467 | 2922 | 22250 | 1197 | 2012 | 18566 | 464618 |
| Peak area value of Seventh peptide fragment ($X_7$) | 8692 | 16816 | 2394 | 101556 | 13991 | 24543 | 84877 | 18875 |
| Peak area value of Eighth peptide fragment ($X_8$) | 7534 | 23335 | 125531 | 1405 | 16063 | 1406 | 37705 | 33511 |
| Peak area value of Ninth peptide fragment ($X_9$) | 3777 | 66744 | 49478 | 7674 | 5324 | 1529 | 32848 | 37098 |
| Peak area value of Alkaline phosphatase (Y) | 268197 | 288388 | 245377 | 208272 | 232234 | 232042 | 272193 | 276191 |

TABLE 5-1

| | Examples | | | |
|---|---|---|---|---|
| | 1 | 2 | 3 | 4 |
| ($X_1$/Y) × 100 | 0.0874 | 0.0746 | 0.0749 | 0.0773 |
| ($X_2$/Y) × 100 | 0.0758 | 0.0746 | 0.0749 | 0.0773 |
| ($X_3$/Y) × 100 | 0.0856 | 0.0843 | 0.1346 | 0.0773 |
| ($X_4$/Y) × 100 | 0.4822 | 0.3293 | 0.6048 | 0.1083 |
| ($X_5$/Y) × 100 | 0.6697 | 0.3536 | 0.6624 | 0.2262 |
| ($X_6$/Y) × 100 | 0.2534 | 0.1367 | 0.2756 | 0.1075 |
| ($X_7$/Y) × 100 | 0.4002 | 0.9830 | 0.1920 | 0.3085 |
| ($X_8$/Y) × 100 | 0.6762 | 0.1928 | 0.9044 | 0.0951 |
| ($X_9$/Y) × 100 | 0.1425 | 0.3506 | 2.2327 | 0.3066 |
| Number of valid spots | 1632 | 1582 | 1577 | 1693 |
| Detection rate (%) | 63 | 61 | 61 | 65 |

TABLE 5-2

| | Comparative Examples | | | | | | | |
|---|---|---|---|---|---|---|---|---|
| | 1 | 2 | 3 | 4 | 5 | 6 | 7 | 8 |
| ($X_1$/Y) × 100 | 4.0791 | 552.7672 | 59.1357 | 7.7495 | 0.6646 | 0.7606 | 4.8257 | 120.5212 |
| ($X_2$/Y) × 100 | 0.2498 | 2.0091 | 1.1990 | 0.1810 | 0.5888 | 0.2035 | 1.6713 | 1.7592 |
| ($X_3$/Y) × 100 | 2.0806 | 221.0835 | 15.4770 | 37.5917 | 1.1462 | 0.2073 | 4.5999 | 41.4217 |
| ($X_4$/Y) × 100 | 0.8497 | 1.1752 | 1.4863 | 0.9060 | 4.6150 | 1.2687 | 3.5158 | 2.4919 |
| ($X_5$/Y) × 100 | 1.6913 | 974.7951 | 2.4228 | 59.6940 | 7.4215 | 2.8110 | 43.6874 | 259.9300 |

TABLE 5-2-continued

|  | Comparative Examples | | | | | | | |
|---|---|---|---|---|---|---|---|---|
|  | 1 | 2 | 3 | 4 | 5 | 6 | 7 | 8 |
| $(X_6/Y) \times 100$ | 0.3915 | 195.7316 | 1.1908 | 10.6831 | 0.5153 | 0.8669 | 6.8208 | 179.6424 |
| $(X_7/Y) \times 100$ | 3.2409 | 5.8310 | 0.9756 | 48.7612 | 6.0247 | 10.5768 | 31.1827 | 7.2979 |
| $(X_8/Y) \times 100$ | 2.8091 | 8.0915 | 51.1585 | 0.6746 | 6.9167 | 0.6061 | 13.8523 | 12.9569 |
| $(X_9/Y) \times 100$ | 1.4083 | 23.1438 | 20.1641 | 3.6846 | 2.2923 | 0.6588 | 12.0681 | 14.3438 |
| Number of valid spots | 1442 | 1080 | 1259 | 1241 | 1211 | 1153 | 1245 | 1205 |
| Detection rate (%) | 56 | 42 | 49 | 48 | 47 | 45 | 48 | 47 |

As shown in Tables 4-1, 4-2, 5-1 and 5-2, when each of the nucleic acid samples prepared by using the alkaline phosphatase compositions of Comparative Examples 1 to 8 was used in the nucleic acid detection method, the number of valid spots was less than 1,500, while, when each of the nucleic acid samples prepared by using the alkaline phosphatase compositions of Examples 1 to 4 was used in the nucleic acid detection method, the number of valid spots was 1,500 or more. The detection rates in Comparative Examples 1 to 8 were different although the alkaline phosphatase specific activities of the alkaline phosphatase compositions were almost the same, while the detection rates in Examples 1 to 4 were almost the same and were higher than the detection rates in Comparative Examples 1 to 8.

As shown in Tables 4-1, 4-2, 5-1 and 5-2, the value of $(X_1/Y) \times 100$, which represents the content ratio of the first peptide fragment to the alkaline phosphatase, was more than 0.6000 for each of the alkaline phosphatase compositions of Comparative Examples 1 to 8 (the minimum value was 0.6646 in the alkaline phosphatase composition of Comparative Example 5), while the value was 0.6000 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $(X_2/Y) \times 100$, which represents the content ratio of the second peptide fragment to the alkaline phosphatase, was more than 0.1800 for each of the alkaline phosphatase compositions of Comparative Examples 1 to 8 (the minimum value was 0.1810 in the alkaline phosphatase composition of Comparative Example 4), while the value was 0.1800 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $(X_3/Y) \times 100$, which represents the content ratio of the third peptide fragment to the alkaline phosphatase, was more than 0.2000 for each of the alkaline phosphatase compositions of Comparative Examples 1 to 8 (the minimum value was 0.2073 in the alkaline phosphatase composition of Comparative Example 6), while the value was 0.2000 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $(X_4/Y) \times 100$, which represents the content ratio of the fourth peptide fragment to the alkaline phosphatase, was more than 0.8000 for each of the alkaline phosphatase compositions of Comparative Examples 1 to 8 (the minimum value was 0.8497 in the alkaline phosphatase composition of Comparative Example 1), while the value was 0.8000 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $(X_5/Y) \times 100$, which represents the content ratio of the fifth peptide fragment to the alkaline phosphatase, was more than 1.6000 for each of the alkaline phosphatase compositions of Comparative Examples 1 to 8 (the minimum value was 1.6913 in the alkaline phosphatase composition of Comparative Example 1), while the value was 1.6000 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $(X_6/Y) \times 100$, which represents the content ratio of the sixth peptide fragment to the alkaline phosphatase, was more than 0.3500 for each of the alkaline phosphatase compositions of Comparative Examples 1 to 8 (the minimum value was 0.3915 in the alkaline phosphatase composition of Comparative Example 1), while the value was 0.3500 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $(X_7/Y) \times 100$, which represents the content ratio of the seventh peptide fragment to the alkaline phosphatase, was more than 1.0000 for each of the alkaline phosphatase compositions of Comparative Examples 1, 2 and 4 to 8 (but 1.0000 or less for Comparative Example 3), while the value was 1.0000 or less for each of the alkaline phosphatase compositions of Examples 1 to 4. This is considered as one of the secondary causes of the difference in the effect between Examples 1 to 4 and Comparative Examples 1, 2 and 4 to 8.

As shown in Tables 4-1, 4-2, 5-1 and 5-2, the value of $(X_8/Y) \times 100$, which represents the content ratio of the eighth peptide fragment to the alkaline phosphatase, was more than 1.0000 for each of the alkaline phosphatase compositions of Comparative Examples 1 to 3, 5, 7 and 8 (but 1.0000 or less for each of Comparative Examples 4 and 6), while the value was 1.0000 or less for each of the alkaline phosphatase compositions of Examples 1 to 4. This is considered as one of the secondary causes of the difference in the effect between Examples 1 to 4 and Comparative Examples 1 to 3, 5, 7 and 8.

As shown in Tables 4-1, 4-2, 5-1 and 5-2, the value of $(X_9/Y) \times 100$, which represents the content ratio of the ninth peptide fragment to the alkaline phosphatase, was more than 2.3000 for each of the alkaline phosphatase compositions of Comparative Examples 2 to 4, 7 and 8 (but 2.3000 or less for each of Comparative Examples 1, 5 and 6), while the value was 2.3000 or less for each of the alkaline phosphatase compositions of Examples 1 to 4. This is considered as one of the secondary causes of the difference in the effect between Examples 1 to 4 and Comparative Examples 2 to 4, 7 and 8.

The invention claimed is:

1. A composition comprising:
   an alkaline phosphatase;
   a first peptide fragment consisting of the amino acid sequence set forth in SEQ ID NO: 1;
   a second peptide fragment consisting of the amino acid sequence set forth in SEQ ID NO: 2;
   a third peptide fragment consisting of the amino acid sequence set forth in SEQ ID NO: 3;
   a fourth peptide fragment consisting of the amino acid sequence set forth in SEQ ID NO: 4;

a fifth peptide fragment consisting of the amino acid sequence set forth in SEQ ID NO: 5; and a sixth peptide fragment consisting of the amino acid sequence set forth in SEQ ID NO: 6, wherein content ratios of the first to sixth peptide fragments to the alkaline phosphatase satisfy formulas (1) to (6), respectively:

$$(X_1/Y) \times 100 \leq 0.6000 \quad (1);$$

$$(X_2/Y) \times 100 \leq 0.1800 \quad (2);$$

$$(X_3/Y) \times 100 \leq 0.2000 \quad (3);$$

$$(X_4/Y) \times 100 \leq 0.8000 \quad (4);$$

$$(X_5/Y) \times 100 \leq 1.6000 \quad (5); \text{ and}$$

$$(X_6/Y) \times 100 \leq 0.3500 \quad (6),$$

wherein $X_1$ to $X_6$ represent peak area values of the first to sixth peptide fragments calculated by an automatic integration method from an extracted ion chromatogram obtained by an LC-MS/MS analysis of the composition, respectively, and Y represents a peak area value of the alkaline phosphatase calculated by an automatic integration method from a chromatogram obtained by an LC-UV analysis of the composition.

2. The composition according to claim 1, wherein:

the composition further comprises a seventh peptide fragment consisting of the amino acid sequence set forth in SEQ ID NO: 7; and a content ratio of the seventh peptide fragment to the alkaline phosphatase satisfies formula (7):

$$(X_7/Y) \times 100 \leq 1.0000 \quad (7),$$

wherein $X_7$ represents a peak area value of the seventh peptide fragment calculated by an automatic integration method from an extracted ion chromatogram obtained by an LC-MS/MS analysis of the composition, and Y is the same as defined above.

3. The composition according to claim 1, wherein:

the composition further comprises an eighth peptide fragment consisting of the amino acid sequence set forth in SEQ ID NO: 8; and a content ratio of the eighth peptide fragment to the alkaline phosphatase satisfies formula (8):

$$(X_8/Y) \times 100 \leq 1.0000 \quad (8),$$

wherein $X_8$ represents a peak area value of the eighth peptide fragment calculated by an automatic integration method from an extracted ion chromatogram obtained by an LC-MS/MS analysis of the composition, and Y is the same as defined above.

4. The composition according to claim 1, wherein:

the composition further comprises a ninth peptide fragment consisting of the amino acid sequence set forth in SEQ ID NO: 9; and a content ratio of the ninth peptide fragment to the alkaline phosphatase satisfies formula (9):

$$(X_9/Y) \times 100 \leq 2.3000 \quad (9),$$

wherein $X_9$ represents a peak area value of the ninth peptide fragment calculated by an automatic integration method from an extracted ion chromatogram obtained by an LC-MS/MS analysis of the composition, and Y is the same as defined above.

5. The composition according to claim 1, wherein the composition has an alkaline phosphatase specific activity of 2,000 U/mg or more.

6. The composition according to claim 1, wherein the alkaline phosphatase is selected from the following (a) and (b):

(a) an alkaline phosphatase comprising a protein molecule consisting of the amino acid sequence set forth in SEQ ID NO: 10; and (b) an alkaline phosphatase comprising a protein molecule consisting of an amino acid sequence that has 70% or more sequence identity to the amino acid sequence set forth in SEQ ID NO: 10 and comprises positions 78 to 90, positions 177 to 187, positions 469 to 477, positions 516 to 528 and positions 534 to 551 of the amino acid sequence set forth in SEQ ID NO: 10.

7. The composition according to claim 6, wherein the amino acid sequence of the protein molecule of the alkaline phosphatase (b) further comprises one or two or more selected from positions 91 to 109, positions 93 to 105 and positions 529 to 531 of the amino acid sequence set forth in SEQ ID NO: 10.

8. The composition according to claim 6, wherein the amino acid sequence of the protein molecule of the alkaline phosphatase (b) further comprises positions 91 to 109 and positions 529 to 531 of the amino acid sequence set forth in SEQ ID NO: 10.

9. The composition according to claim 1, wherein the composition further comprises a nucleic acid, and is a composition used for dephosphorylating the nucleic acid.

10. The composition according to claim 1, wherein the composition further comprises a dephosphorylated nucleic acid, and is a composition used for preparing a labeled nucleic acid comprising the dephosphorylated nucleic acid and a labeling substance bound to the dephosphorylated nucleic acid.

11. The composition according to claim 1, wherein the composition further comprises a labeled nucleic acid comprising a dephosphorylated nucleic acid and a labeling substance bound to the dephosphorylated nucleic acid, and is a nucleic acid sample to be subjected to a nucleic acid detection method.

12. The composition according to claim 11, wherein the nucleic acid detection method is a nucleic acid detection method using a nucleic acid microarray.

13. A method of producing a dephosphorylated nucleic acid, the method comprising:

providing the composition according to claim 1;

providing a nucleic acid; and treating the nucleic acid with the composition to dephosphorylate the nucleic acid.

14. A method of producing a labeled nucleic acid, the method comprising:

providing the composition according to claim 1;

providing a nucleic acid;

providing a labeling substance;

treating the nucleic acid with the composition to dephosphorylate the nucleic acid; and binding the labeling substance to the dephosphorylated nucleic acid.

* * * * *